United States Patent
Haefner et al.

(10) Patent No.: US 7,499,750 B2
(45) Date of Patent: Mar. 3, 2009

(54) NOISE CANCELING CARDIAC ELECTRODES

(75) Inventors: Paul Haefner, Circle Pines, MN (US); Darrell Orvin Wagner, Isanti, MN (US); Jason Alan Shiroff, Shoreview, MN (US); Marina Brockway, Shoreview, MN (US); Apurv Kamath, Solana Beach, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 640 days.

(21) Appl. No.: 10/738,608

(22) Filed: Dec. 17, 2003

(65) Prior Publication Data

US 2004/0230243 A1    Nov. 18, 2004

Related U.S. Application Data

(60) Provisional application No. 60/462,272, filed on Apr. 11, 2003.

(51) Int. Cl.
*A61B 5/04*   (2006.01)
*A61N 1/08*   (2006.01)
*A61N 1/37*   (2006.01)

(52) U.S. Cl. ............... 607/27; 607/62; 600/509

(58) Field of Classification Search ......... 600/508, 600/509; 128/901, 902; 607/2, 13, 27, 62, 607/63

See application file for complete search history.

(56) References Cited

U.S. PATENT DOCUMENTS

| | | | |
|---|---|---|---|
| 4,091,818 A * | 5/1978 | Brownlee et al. | ............. 607/9 |
| 4,414,982 A | 11/1983 | Durkan | |
| 4,562,841 A | 1/1986 | Brockway et al. | |
| 4,813,427 A | 3/1989 | Schlaefke et al. | |
| 4,827,935 A | 5/1989 | Geddes et al. | |
| 4,830,008 A | 5/1989 | Meer | |
| 4,836,219 A | 6/1989 | Hobson et al. | |
| 4,856,524 A | 8/1989 | Baker, Jr. | |
| 4,928,688 A | 5/1990 | Mower | |
| 4,953,551 A | 9/1990 | Mehra et al. | |

(Continued)

FOREIGN PATENT DOCUMENTS

EP    0750920    1/1997

(Continued)

OTHER PUBLICATIONS

Renee Hartz et al., *New Approach to Defibrillator Insertion*, J. Thoracic Cardiovascular Surgery, vol. 97, pp. 920-922 (1989).

(Continued)

*Primary Examiner*—Carl H Layno
*Assistant Examiner*—Natasha N Patel
(74) *Attorney, Agent, or Firm*—Hollingsworth & Funk, LLC

(57) ABSTRACT

Implementing a subcutaneous medical electrode system involves positioning a number of electrode subsystems in relation to a heart so that noise cancellation provides an improved signal to noise ratio of the cardiac signal and/or to provide one electrode arrangement preferential for cardiac signals and another arrangement preferential for noise signals. One of the electrode subsystems so positioned may include one or more can electrodes located on a housing enclosing a medical device. The medical device may be configured to provide therapeutic, diagnostic, or monitoring functions, including, for example, cardiac arrhythmia therapy.

42 Claims, 19 Drawing Sheets

U.S. PATENT DOCUMENTS

| | | | |
|---|---|---|---|
| 5,024,222 A | 6/1991 | Thacker | |
| 5,036,849 A | 8/1991 | Hauck et al. | |
| 5,105,354 A | 4/1992 | Nishimura | |
| 5,133,353 A | 7/1992 | Hauser | |
| 5,146,918 A | 9/1992 | Kallok et al. | |
| 5,170,784 A | 12/1992 | Ramon et al. | |
| 5,178,156 A | 1/1993 | Takishima et al. | |
| 5,179,945 A | 1/1993 | Van Hofwegen et al. | |
| 5,187,657 A | 2/1993 | Forbes | |
| 5,203,348 A | 4/1993 | Dahl et al. | |
| 5,209,229 A | 5/1993 | Gilli | |
| 5,211,173 A | 5/1993 | Kallok et al. | |
| 5,215,082 A | 6/1993 | Kallok et al. | |
| 5,230,337 A | 7/1993 | Dahl et al. | |
| 5,233,983 A | 8/1993 | Markowitz | |
| 5,245,995 A | 9/1993 | Sullivan et al. | |
| 5,261,400 A | 11/1993 | Bardy | |
| 5,280,791 A | 1/1994 | Lavie | |
| 5,284,136 A | 2/1994 | Hauck et al. | |
| 5,292,338 A | 3/1994 | Bardy | |
| 5,299,118 A | 3/1994 | Martens et al. | |
| 5,300,106 A | 4/1994 | Dahl et al. | |
| 5,301,677 A | 4/1994 | Hsung | |
| 5,313,953 A | 5/1994 | Yomtov et al. | |
| 5,314,430 A | 5/1994 | Bardy | |
| 5,314,459 A | 5/1994 | Swanson et al. | |
| 5,318,597 A | 6/1994 | Hauck et al. | |
| 5,331,966 A | 7/1994 | Bennett et al. | |
| 5,334,222 A | 8/1994 | Salo et al. | |
| 5,335,657 A | 8/1994 | Terry, Jr. et al. | |
| 5,360,442 A | 11/1994 | Dahl et al. | |
| 5,366,496 A | 11/1994 | Dahl et al. | |
| 5,372,606 A | 12/1994 | Lang et al. | |
| 5,376,103 A | 12/1994 | Anderson et al. | |
| 5,376,106 A | 12/1994 | Stahmann et al. | |
| 5,376,476 A | 12/1994 | Eylon | |
| 5,388,578 A | 2/1995 | Yomtov et al. | |
| 5,391,200 A | 2/1995 | KenKnight et al. | |
| 5,397,342 A | 3/1995 | Heil, Jr. et al. | |
| 5,411,031 A | 5/1995 | Yomtov | |
| 5,411,525 A | 5/1995 | Swanson et al. | |
| 5,411,539 A | 5/1995 | Neisz | |
| 5,439,482 A | 8/1995 | Adams et al. | |
| 5,441,518 A | 8/1995 | Adams et al. | |
| 5,466,245 A | 11/1995 | Spinelli et al. | |
| 5,468,254 A | 11/1995 | Hahn et al. | |
| 5,476,485 A * | 12/1995 | Weinberg et al. | 607/28 |
| 5,483,969 A | 1/1996 | Testerman et al. | |
| 5,485,851 A | 1/1996 | Erickson | |
| 5,520,176 A | 5/1996 | Cohen | |
| 5,520,191 A | 5/1996 | Karlsson et al. | |
| 5,522,862 A | 6/1996 | Testerman et al. | |
| 5,531,779 A | 7/1996 | Dahl et al. | |
| 5,540,727 A | 7/1996 | Tockman et al. | |
| 5,545,186 A | 8/1996 | Olson et al. | |
| 5,545,202 A | 8/1996 | Dahl et al. | |
| 5,549,655 A | 8/1996 | Erickson | |
| 5,601,607 A | 2/1997 | Adams | |
| 5,603,732 A | 2/1997 | Dahl et al. | |
| 5,620,466 A | 4/1997 | Haefner et al. | |
| 5,634,938 A | 6/1997 | Swanson et al. | |
| 5,641,326 A | 6/1997 | Adams | |
| 5,645,570 A | 7/1997 | Corbucci | |
| 5,662,688 A | 9/1997 | Haefner et al. | |
| 5,697,953 A | 12/1997 | Kroll et al. | |
| 5,704,365 A * | 1/1998 | Albrecht et al. | 600/515 |
| 5,713,355 A * | 2/1998 | Richardson et al. | 600/336 |
| 5,713,933 A | 2/1998 | Condie et al. | |
| 5,724,984 A | 3/1998 | Arnold et al. | |
| 5,738,102 A | 4/1998 | Lemelson | |
| 5,792,188 A | 8/1998 | Starkweather et al. | |
| 5,802,188 A | 9/1998 | McDonough | |
| 5,814,087 A | 9/1998 | Renirie | |
| 5,827,326 A | 10/1998 | Kroll et al. | |
| 5,836,987 A | 11/1998 | Baumann et al. | |
| 5,844,680 A | 12/1998 | Sperling | |
| 5,855,593 A | 1/1999 | Olson et al. | |
| 5,891,023 A | 4/1999 | Lynn | |
| 5,895,414 A | 4/1999 | Sanchez-Zambrano | |
| 5,902,250 A | 5/1999 | Verrier et al. | |
| 5,911,218 A | 6/1999 | DiMarco | |
| 5,916,243 A | 6/1999 | KenKnight et al. | |
| 5,944,680 A | 8/1999 | Christopherson et al. | |
| 5,957,956 A | 9/1999 | Kroll et al. | |
| 5,964,778 A | 10/1999 | Fugoso et al. | |
| 5,970,975 A | 10/1999 | Estes et al. | |
| 5,974,340 A | 10/1999 | Kadhiresan | |
| 5,981,011 A | 11/1999 | Overcash et al. | |
| 5,997,526 A * | 12/1999 | Giba et al. | 604/531 |
| 6,026,320 A | 2/2000 | Carlson et al. | |
| 6,044,298 A | 3/2000 | Salo et al. | |
| 6,055,454 A | 4/2000 | Heemels | |
| 6,059,725 A | 5/2000 | Steinschneider | |
| 6,064,910 A | 5/2000 | Andersson et al. | |
| 6,076,015 A | 6/2000 | Hartley et al. | |
| 6,091,973 A | 7/2000 | Colla et al. | |
| 6,091,986 A | 7/2000 | Keimel | |
| 6,099,479 A | 8/2000 | Christopherson et al. | |
| 6,115,628 A | 9/2000 | Stadler et al. | |
| 6,120,441 A | 9/2000 | Griebel | |
| 6,126,611 A | 10/2000 | Bourgeois et al. | |
| 6,128,534 A | 10/2000 | Park et al. | |
| 6,132,384 A | 10/2000 | Christopherson et al. | |
| 6,141,581 A | 10/2000 | Olson et al. | |
| 6,141,590 A | 10/2000 | Renirie et al. | |
| 6,148,230 A | 11/2000 | KenKnight | |
| 6,148,233 A * | 11/2000 | Owen et al. | 607/5 |
| 6,190,326 B1 | 2/2001 | McKinnon et al. | |
| 6,200,265 B1 | 3/2001 | Walsh et al. | |
| 6,205,357 B1 | 3/2001 | Ideker et al. | |
| 6,221,011 B1 | 4/2001 | Bardy | |
| 6,227,072 B1 | 5/2001 | Ritchey et al. | |
| 6,240,316 B1 | 5/2001 | Richmond et al. | |
| 6,251,126 B1 | 6/2001 | Ottenhoff et al. | |
| 6,258,039 B1 | 7/2001 | Okamoto et al. | |
| 6,259,947 B1 | 7/2001 | Olson et al. | |
| 6,269,269 B1 | 7/2001 | Ottenhoff et al. | |
| 6,270,457 B1 | 8/2001 | Bardy | |
| 6,272,377 B1 | 8/2001 | Sweeney et al. | |
| 6,273,856 B1 | 8/2001 | Sun et al. | |
| 6,275,727 B1 | 8/2001 | Hopper et al. | |
| 6,277,072 B1 | 8/2001 | Bardy | |
| 6,280,380 B1 | 8/2001 | Bardy | |
| 6,280,462 B1 | 8/2001 | Hauser et al. | |
| 6,285,907 B1 | 9/2001 | Kramer et al. | |
| 6,312,378 B1 | 11/2001 | Bardy | |
| 6,327,499 B1 | 12/2001 | Alt | |
| 6,336,903 B1 | 1/2002 | Bardy | |
| 6,351,669 B1 | 2/2002 | Hartley et al. | |
| 6,351,670 B1 | 2/2002 | Kroll | |
| 6,351,673 B1 | 2/2002 | Ding et al. | |
| 6,353,759 B1 | 3/2002 | Hartley et al. | |
| 6,358,203 B2 | 3/2002 | Bardy | |
| 6,360,127 B1 | 3/2002 | Ding et al. | |
| 6,361,494 B1 | 3/2002 | Lindenthaler | |
| 6,363,270 B1 | 3/2002 | Colla et al. | |
| 6,368,284 B1 | 4/2002 | Bardy | |
| 6,368,287 B1 | 4/2002 | Hadas | |
| 6,371,922 B1 | 4/2002 | Baumann et al. | |
| 6,375,621 B1 | 4/2002 | Sullivan | |
| 6,398,728 B1 | 6/2002 | Bardy | |
| 6,405,085 B1 | 6/2002 | Graupner et al. | |
| 6,409,675 B1 | 6/2002 | Turcott | |
| 6,411,848 B2 | 6/2002 | Kramer et al. | |

| | | |
|---|---|---|
| 6,415,174 B1 | 7/2002 | Bebehani et al. |
| 6,424,865 B1 | 7/2002 | Ding |
| 6,438,407 B1 | 8/2002 | Ousdigian et al. |
| 6,438,410 B2 | 8/2002 | Hsu et al. |
| 6,440,066 B1 | 8/2002 | Bardy |
| 6,449,503 B1 | 9/2002 | Hsu |
| 6,459,929 B1 | 10/2002 | Hopper et al. |
| 6,463,325 B1 | 10/2002 | Bolz |
| 6,480,733 B1 | 11/2002 | Turcott |
| 6,487,443 B2 | 11/2002 | Olson et al. |
| 6,490,485 B1 | 12/2002 | Sun et al. |
| 6,491,639 B1 | 12/2002 | Turcott |
| 6,491,675 B1 | 12/2002 | Shimada et al. |
| 6,496,715 B1 | 12/2002 | Lee et al. |
| 6,505,067 B1 | 1/2003 | Lee et al. |
| 6,512,940 B1 | 1/2003 | Brabec et al. |
| 6,522,915 B1 | 2/2003 | Ceballos et al. |
| 6,564,106 B2 | 5/2003 | Guck et al. |
| 6,574,507 B1 | 6/2003 | Bonnet |
| 6,584,351 B1 * | 6/2003 | Ekwall ................ 607/9 |
| 6,589,188 B1 | 7/2003 | Street et al. |
| 6,597,951 B2 | 7/2003 | Kramer et al. |
| 6,607,509 B2 | 8/2003 | Bobroff et al. |
| 6,615,083 B2 | 9/2003 | Kupper |
| 6,622,046 B2 | 9/2003 | Fraley et al. |
| 6,641,542 B2 | 11/2003 | Cho et al. |
| 6,752,765 B1 | 6/2004 | Jensen et al. |
| 6,752,766 B2 | 6/2004 | Kowallik et al. |
| 6,760,615 B2 | 7/2004 | Ferek-Petric |
| 6,766,190 B2 | 7/2004 | Ferek-Petric |
| 6,773,404 B2 | 8/2004 | Poezevera et al. |
| 6,810,287 B2 | 10/2004 | Zhu et al. |
| 6,823,214 B1 | 11/2004 | Sun et al. |
| 6,839,593 B1 | 1/2005 | Sun et al. |
| 6,881,192 B1 | 4/2005 | Park |
| 6,904,320 B2 | 6/2005 | Park et al. |
| 6,928,324 B2 | 8/2005 | Park et al. |
| 6,988,498 B2 | 1/2006 | Berthon-Jones et al. |
| 7,016,730 B2 | 3/2006 | Ternes |
| 7,092,755 B2 | 8/2006 | Florio |
| 7,155,278 B2 | 12/2006 | King et al. |
| 7,215,890 B2 | 5/2007 | Tegger, Jr. et al. |
| 7,260,432 B2 | 8/2007 | Kramer et al. |
| 2001/0031930 A1 | 10/2001 | Roizen et al. |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082658 A1 | 6/2002 | Heinrich et al. |
| 2002/0085741 A1 | 7/2002 | Shimizu |
| 2002/0091414 A1 | 7/2002 | Bardy et al. |
| 2002/0095184 A1 | 7/2002 | Bardy et al. |
| 2002/0103510 A1 | 8/2002 | Bardy et al. |
| 2002/0107544 A1 | 8/2002 | Ostroff et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0120311 A1 | 8/2002 | Lindh et al. |
| 2002/0136328 A1 | 9/2002 | Shimizu |
| 2002/0143264 A1 | 10/2002 | Ding et al. |
| 2002/0193697 A1 | 12/2002 | Cho et al. |
| 2002/0193839 A1 | 12/2002 | Cho et al. |
| 2003/0004546 A1 | 1/2003 | Casey |
| 2003/0004552 A1 | 1/2003 | Plombon et al. |
| 2003/0023175 A1 | 1/2003 | Arzbaecher et al. |
| 2003/0023184 A1 | 1/2003 | Pitts-Crick et al. |
| 2003/0036778 A1 | 2/2003 | Ostroff et al. |
| 2003/0045904 A1 | 3/2003 | Bardy et al. |
| 2003/0055461 A1 | 3/2003 | Girouard et al. |
| 2003/0069609 A1 | 4/2003 | Thompson |
| 2003/0083587 A1 | 5/2003 | Ferek-Petric |
| 2003/0088278 A1 | 5/2003 | Bardy et al. |
| 2003/0088279 A1 | 5/2003 | Rissmann et al. |
| 2003/0088280 A1 | 5/2003 | Ostroff |
| 2003/0088281 A1 | 5/2003 | Ostroff et al. |
| 2003/0088282 A1 | 5/2003 | Ostroff |
| 2003/0088283 A1 | 5/2003 | Ostroff |
| 2003/0088286 A1 | 5/2003 | Ostroff et al. |
| 2003/0097153 A1 | 5/2003 | Bardy et al. |
| 2003/0100925 A1 | 5/2003 | Pape et al. |
| 2003/0153953 A1 | 8/2003 | Park et al. |
| 2003/0153954 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0187336 A1 | 10/2003 | Odagiri et al. |
| 2003/0195571 A1 | 10/2003 | Burnes et al. |
| 2003/0199945 A1 | 10/2003 | Ciulla |
| 2003/0204146 A1 | 10/2003 | Carlson |
| 2003/0204213 A1 | 10/2003 | Jensen et al. |
| 2003/0212436 A1 | 11/2003 | Brown |
| 2003/0216789 A1 | 11/2003 | Deem et al. |
| 2004/0002742 A1 | 1/2004 | Florio |
| 2004/0030362 A1 | 2/2004 | Hill et al. |
| 2004/0088027 A1 | 5/2004 | Burnes et al. |
| 2004/0102814 A1 | 5/2004 | Sorensen et al. |
| 2004/0111021 A1 | 6/2004 | Olson |
| 2004/0111040 A1 | 6/2004 | Ni et al. |
| 2004/0138719 A1 | 7/2004 | Cho et al. |
| 2004/0176809 A1 | 9/2004 | Cho et al. |
| 2004/0210155 A1 | 10/2004 | Takemura et al. |
| 2004/0230230 A1 | 11/2004 | Lindstrom et al. |
| 2004/0230243 A1 | 11/2004 | Haefner |
| 2004/0243012 A1 | 12/2004 | Ciaccio et al. |
| 2005/0039745 A1 | 2/2005 | Stahmann et al. |
| 2005/0042589 A1 | 2/2005 | Hatlestad et al. |
| 2005/0043644 A1 | 2/2005 | Stahmann et al. |
| 2005/0137632 A1 | 6/2005 | Ding et al. |
| 2007/0161873 A1 | 7/2007 | Ni et al. |
| 2007/0282215 A1 | 12/2007 | Ni et al. |

FOREIGN PATENT DOCUMENTS

| | | |
|---|---|---|
| EP | 0770407 | 5/1997 |
| EP | 0940155 | 9/1999 |
| EP | 1038498 | 9/2000 |
| EP | 1151718 | 11/2001 |
| EP | 1162125 | 12/2001 |
| EP | 1172125 | 1/2002 |
| EP | 1317943 | 6/2003 |
| WO | WO8402080 | 7/1984 |
| WO | WO9203983 | 3/1992 |
| WO | WO9217240 | 10/1992 |
| WO | WO 92/20402 | 11/1992 |
| WO | WO9904841 | 4/1999 |
| WO | WO0001438 | 1/2000 |
| WO | WO02087696 | 11/2002 |

| WO | WO03003905 | 1/2003 |

OTHER PUBLICATIONS

Theofilos M. Kolettis, MD, PhD et al., *Sumammary Implantation of a Cardioverter-Defibrillator with a Nonthoractomy Lead System*, Am. Heart J., vol. 126, pp. 1222-1223 (Nov. 1993).

John C. Schuder et al., *Transthoracic Ventricular Defibrillation in the Dog with Truncated and Untruncated Exponential Stimuli*, IEEE Trans. On Bio-Medical Engin., vol. BME-18, No. 6, pp. 410-415 (Nov. 1971).

John C. Schuder et al., *Ventricular Defibrillation in the Dog Using Implanted and Partially Implanted Electrode Systems*, Am. J. of Cardiology, vol. 33, pp. 243-247 (Feb. 1974).

John C. Schuder et al., *Experimental Ventricular Defibrillation with an Automatic and Completely Implanted System*, Trans. Am. Soc. Artif. Int. Organs, vol. 16, pp. 207-212 (1970).

Karel Smits & Marek Malik, *Defibrillation Threshold (DFT) Model of a Fully Subcutaneous ICD System*, Europace Supplements, vol. 2, Jun. 2001 at B83.

Stirbis et al., *Optmizing the Shape of Implanted Artificial Pacemakers*, Kaunas Medical Institute. Translated from Meditsinskaya Tekhnika, No. 6, pp. 25-27 (1986).

Charles T. Leng et al., *Lead Configuration for Defibrillator Implantation in a Patient with Congenital Heart Disease and a Mechanical Prosthetic Tricuspid Valve*, Pace, vol. 24, No. 8, pp. 1291-1292 (Aug. 2001).

Park & Pollock, *Use of an Implantable Cardioverter Defibrillator in an Eight-Month-Old Infant with Ventricular Fibrillation Arising from a Myocardial Fibroma*, Pace, vol. 22, No. 1, pp. 138-139 (Jan. 1999).

Rainer Gradaus M.D. et al., *Nonthoracotomy Implantable Cardioverter Defibrillator Placement in Children: Use of a Subcutaneous Array Leads and Abdominally Placed Implantable Cardioverter Defibrillators in Children*, J. of Cardiovascular Electrophysiology, vol. 12, No. 3, pp. 356-360 (Mar. 2001).

Aircraft Noise and Sleep Disturbance: Final Report, prepared by the Civil Aviation Authority London on behalf of the Department of Trade, Aug. 1980 (CAA Report).

Ajilore et al., Nightcap: Laboratory and home-based evaluation of a portable sleep monitor, 32 Psychophysiology, 32-98, 1995. Abstract only.

Balaban et al., Feasibility of Screening for Sleep Apnea using Pacemaker Impedance Sensor, Cleveland Clin. Fdn, Cleveland, OH, Medtronic, Inc., Minneapolis, MN, Strong Memorial Hosp., Rochester, NY and Univ. Hosp., Zurich, Switzerland, Pace, vol. 24, pp. 617, Apr. 2001. Abstract only.

Belouchrani et al., Blind Source Separation Based on Time-Frequency Signal Representations, IEEE Transactions on Signal Processing, vol. 46, No. 11, pp. 2888-2897, Nov. 1998.

Bradley et al., Pathophysiologic and Therapeutic Implications of Sleep Apnea in Congestive Heart Failure, J Cardiac Failure 2, No. 3, pp. 223-240, 1996.

Comon, Independent component analysis, A new concept?, Signal Processing, vol. 36, No. 3, pp. 287-314, Apr. 1994.

Gallois et al., Multi-Channel Analysis of the EEG Signals and Statistic Particularities for Epileptic Seizure Forecast, Second Joint EMBS/BMES Conference, pp. 208-215, Oct. 23-26, 2002.

Garrigue et al., Benefit of Atrial Pacing in Sleep Apnea Syndrome, N. Engl. J. Med., vol. 346, No. 6, pp. 404-412, Feb. 7, 2002.

Garrigue et al., Night Atrial Overdrive with DDD Pacing: A New Therapy for Sleep Apnea Syndrome, Hopital Cardiologique du Haut-Leveque, University of Bordeaux, Pessac-Bordeaux, France, Pace, vol. 23, p. 700, Apr. 2000. Abstract only.

Garrigue et al., Night Atrial Overdrive with DDD Pacing Results in a Significant Reduction of Sleep Apnea Episodes and QOL Improvement in Heart Failure Patients, Hosp. Cardiologique du Haut-Leveque, Bordeaux-Pessac, France, Abstract Session 25, No. 145, Pace, vol. 24, p. 575, Apr. 2001. Abstract only.

Hilton et al., Evaluation of Frequency and Time-frequency Spectral Analysis of Heart Rate Variability as a Diagnostic Marker of the Sleep Apnea Syndrome, Med Biol Eng Comput Nov. 1999, 37(6), 760-9. Abstract only.

Hyvärinen et al., Independent Component Analysis: A Tutorial, Helsinki Univ. of Technology, pp. 1-31, Apr. 1999.

Javaheri et al., A Mechanism of Central Sleep Apnea In Patients With Heart Failure, New England Journal of Medicine, Sep. 1999; 341(13):949-54.

Javaheri et al., Sleep Apnea in 81 Ambulatory Male Patients with Stable Heart Failure, from the Sleep Disorders Laboratory, Department of Veterans Affairs Medical Center, and the Department of Medicine, University of Cincinnati College of Medicine, Cincinnati, OH, pp. 2154-2159, Nov. 20, 1997.

Krahn et al. Recurrent syncope. Experience with an implantable loop record. Cardiol. Clin., vol. 15(2), May 1997, pp. 316-326 Abstract only.

Mettauer et al., VO2 kinetics reveal a central limitation at the onset of subthreshold exercise in heart transplant recipients. J Applied Physiology 88:1228-1238, 2000.

Rieta, et al., Atrial Activity Extraction Based on Blind Source Separation as an Alternative to QRST Cancellation for Atrial Fibrillation Analysis, Computers in Cardiology, vol. 27, pp. 69-72, 2000.

Roche et al., Screening of Obstructive Sleep Apnea Syndrome by Heart Rate Variability Analysis, Circulation Sep. 28, 1999; 100(13):1411-5.

Vanninen et al., Cardiac Sympathovagal Balance During Sleep Apnea Episodes, Clin Physiol May 1996; 16(3):209-16.

Verrier et al., Sleep, dreams, and sudden death: the case for sleep as an autonomic stress test for the heart, 31 Cardiovascular Research 181-211, 1996.

Verrier et al., Sleep Related Cardiovascular Risk: New Home-Based Monitoring Technology for Improved Diagnosis and Therapy, 2 A.N. E. 158-175, 1997.

Waldemark et al., Detection and Apnea Using Short Window FFT Technique and Artificial Neural Network, SPIE, International Society for Optical Engineering, vol. 3390, pp. 122-133, 1998.

Young et al., The Occurrence of Sleep-disordered Breathing Among Middle-aged Adults, The New England Journal of Medicine, vol. 328, No. 17, pp. 1230-1235, Apr. 29, 1993.

Zarzoso et al., Blind Separation of Independent Sources for Virtually Any Source Probability Density Function, IEEE Transactions on Signal Processing, vol. 47, No. 9, pp. 2419-2432, Sep. 1999.

Zarzoso et al., Noninvasive Fetal Electrocardiogram Extraction: Blind Separation Versus Adaptive Noise Cancellation, IEEE Transactions on Biomedical Engineering, vol. 48, No. 1, pp. 12-18, Jan. 2001.

* cited by examiner

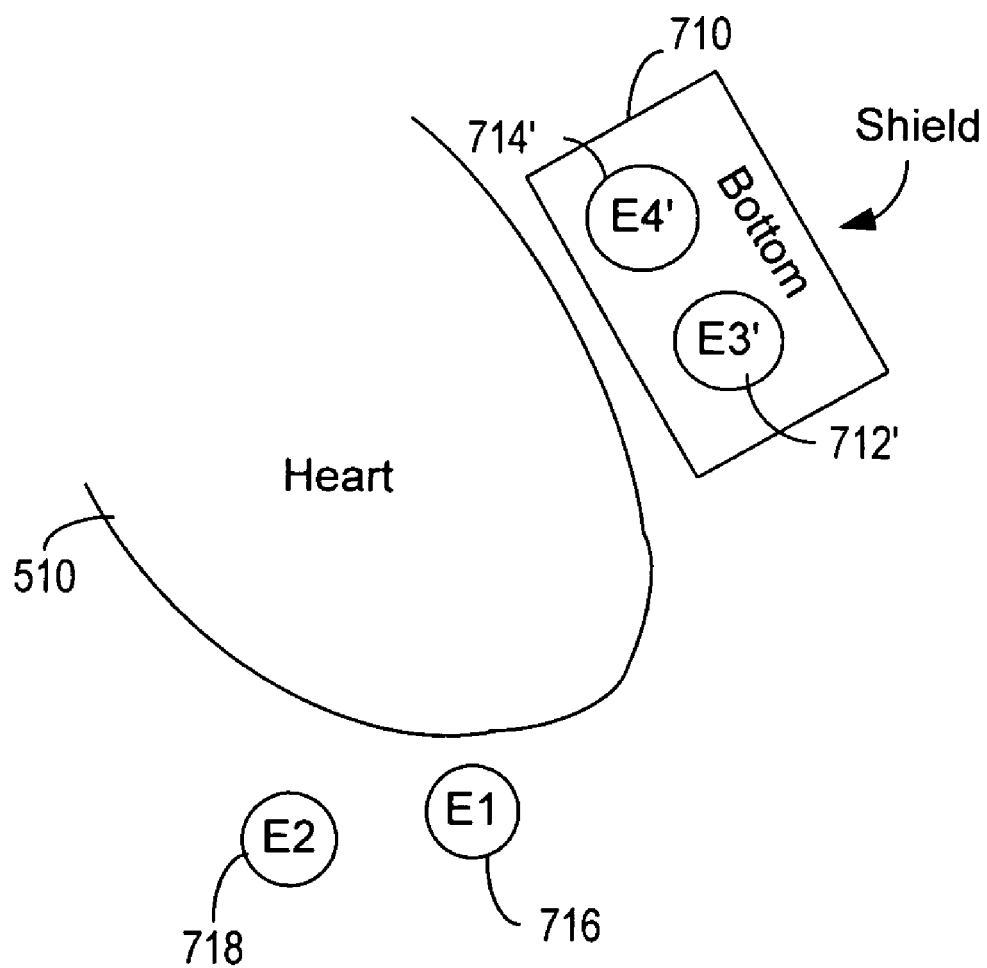

NOISE CANCELING CARDIAC ELECTRODES

RELATED APPLICATIONS

This application claims the benefit of Provisional Patent Application Ser. No. 60/462,272, filed on Apr. 11, 2003, to which priority is claimed pursuant to 35 U.S.C. §119(e) and which is hereby incorporated herein by reference.

FIELD OF THE INVENTION

The present invention relates generally to implantable medical devices and, more particularly, to electrode configurations for noise cancellation.

BACKGROUND OF THE INVENTION

The healthy heart produces regular, synchronized contractions. Rhythmic contractions of the heart are normally controlled by the sinoatrial (SA) node, which is a group of specialized cells located in the upper right atrium. The SA node is the normal pacemaker of the heart, typically initiating 60-100 heartbeats per minute. When the SA node is pacing the heart normally, the heart is said to be in normal sinus rhythm.

If the heart's electrical activity becomes uncoordinated or irregular, the heart is denoted to be arrhythmic. Cardiac arrhythmia impairs cardiac efficiency and can be a potential life-threatening event. Cardiac arrythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid contractions of the atria. Besides being hemodynamically inefficient, the rapid contractions of the atria can also adversely affect the ventricular rate.

Ventricular tachycardia occurs, for example, when electrical activity arises in the ventricular myocardium at a rate more rapid than the normal sinus rhythm. Ventricular tachycardia can quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

Typical implantable cardioverter/defibrillators (ICDs) include one or more endocardial leads to which at least one defibrillation electrode is connected. Such ICDs are capable of delivering high-energy shocks to the heart, interrupting the ventricular tachyarrhythmia or ventricular fibrillation, and allowing the heart to resume normal sinus rhythm. ICDs may also include pacing functionality.

Although ICDs are very effective at preventing Sudden Cardiac Death (SCD), most people at risk of SCD are not provided with implantable defibrillators. Primary reasons for this unfortunate reality include the limited number of physicians qualified to perform transvenous lead/electrode implantation, a limited number of surgical facilities adequately equipped to accommodate such cardiac procedures, and a limited number of the at-risk patient population that may safely undergo the required endocardial or epicardial lead/electrode implant procedure. Subcutaneous ICDs are being developed to address these issues.

There is a need for improved electrode configurations specific to the needs of subcutaneous electrode placement and to address the noise associated with subcutaneous electrode placement. There is a further need for a method of improving the signal to noise ratio of the cardiac signal in subcutaneous ICD's. The present invention fulfills these and other needs, and addresses deficiencies in known systems and techniques.

SUMMARY OF THE INVENTION

The present invention is directed to cardiac monitoring and/or stimulation methods and systems that, in general, provide transthoracic monitoring, defibrillation therapies, pacing therapies, or a combination of these capabilities. Embodiments of the present invention include those directed to subcutaneous cardiac monitoring and/or stimulation methods and systems that detect and/or treat cardiac arrhythmia.

According to one embodiment of the invention, a medical system includes a housing having a medical device disposed within the housing. The medical device is coupled to subcutaneous noise canceling electrode subsystems positioned relative to a heart so that the signal to noise ratio of the cardiac signal is improved.

In another embodiment of the invention, a cardiac stimulator includes a pulse generator with a controller and a number of implantable electrodes communicatively coupled to the pulse generator. The electrodes are arranged in a spaced relationship with respect to cardiac tissue and vasculature for transthoracic cardiac sensing and energy delivery. The plurality of electrodes include a first combination of electrodes adapted to preferentially sense cardiac signals and a second combination of electrodes adapted to preferentially sense noise signals.

In a further embodiment, the controller selects a first combination of electrodes as an electrode combination that provides a cardiac signal response that exceeds a threshold, and selects a second combination of electrodes as an electrode combination that provides a noise component response. The ICD may then use these combinations to reduce noise and provide improved signal-to-noise ratios of sensed cardiac signals.

In yet another embodiment, a first electrode combination may comprise n electrodes positioned at a first location relative to a patient's heart and at least n+1 electrodes positioned at a second location relative to the patient's heart, where n is an integer equal to or greater than 1. Spatially diverse and separate electrodes and/or electrode elements may be used to increase the signal-to-noise ratio (SNR) of sensed signals. Orthogonal sets or spatially separate combinations of electrodes and/or electrode elements may also be used to increase the SNR of cardiac signals in accordance with the present invention.

In another embodiment of the present invention, a cardiac stimulator includes a pulse generator with a controller and a plurality of surface electrodes communicatively coupled to the pulse generator and arranged in a spaced relationship with respect to cardiac tissue and vasculature for transthoracic cardiac sensing and energy delivery. Various electrode spacings and configurations that provide noise cancellation may be used in combinations adapted to preferentially sense cardiac signals and noise signals to increase the desired cardiac SNR.

The present invention also contemplates employment of noise canceling multi-element electrode configurations having shapes adapted to provide enhanced noise cancellation. Useful electrode configurations include circular, elliptical, polygonal, curved, hook or arrow shaped configurations.

In yet another embodiment of the present invention, a method of sensing cardiac activity involves providing a plurality of implantable electrodes, wherein each of the electrodes arranged in a spaced relationship with respect to cardiac tissue and vasculature for transthoracic cardiac sensing and energy delivery. The electrodes are selectively combinable to define a plurality of sensing vectors. The method further involves selecting a first sensing vector of the plurality of sensing vectors which is preferentially sensitive to signals associated with the cardiac activity, and selecting a second sensing vector of the plurality of sensing vectors which is preferentially sensitive to noise signals. The method may also involve selecting combinations of electrodes that provide for enhanced noise cancellation and selecting orthogonal electrode sets.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 4A, 4B, 4C, and 4D are examples of configurations of noise canceling electrodes in accordance with the present invention, wherein at least one pair of electrodes is shielded;

Figure 1A:
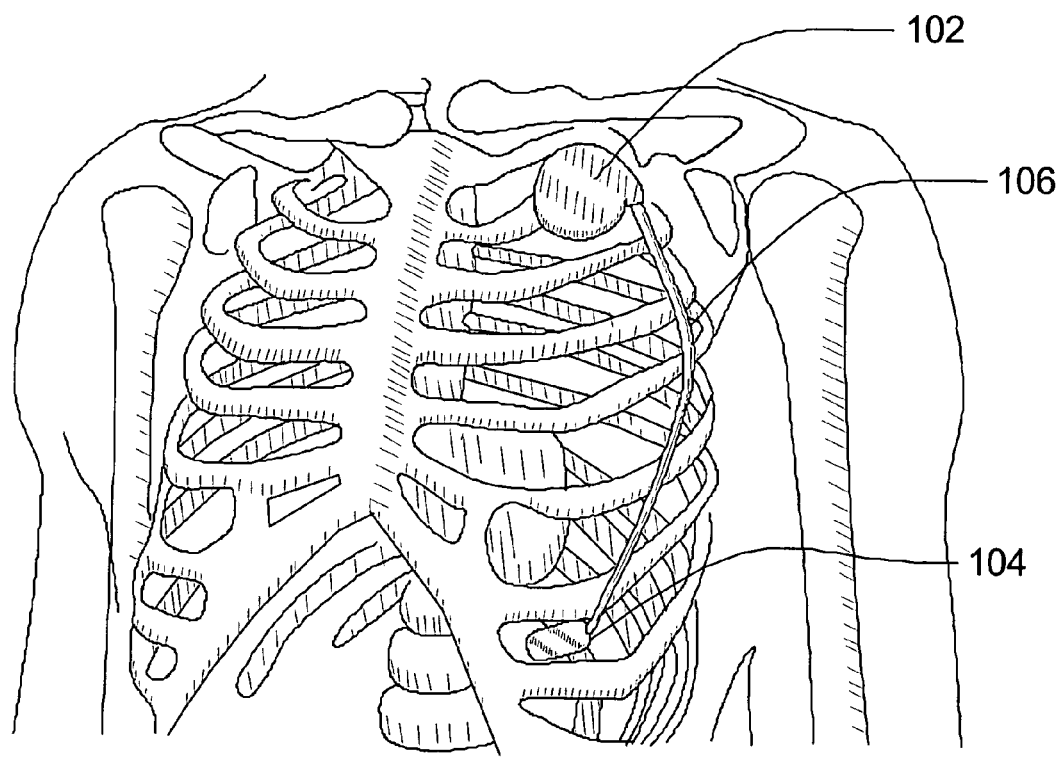
FIGS. 1A and 1B are views of a transthoracic cardiac sensing and/or stimulation device as implanted in a patient in accordance with an embodiment of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device according to the present invention can include one or more of the features, structures, methods, or combinations thereof described hereinbelow. For example, a cardiac monitor or a cardiac stimulator can be implemented to include one or more of the advantageous features and/or processes described below. It is intended that such a monitor, stimulator, or other implanted or partially implanted device need not include all of the features described herein, but can be implemented to include selected features that provide for unique structures and/or functionality. Such a device may be implemented to provide a variety of therapeutic or diagnostic functions.

In general terms, implantable noise canceling electrodes or leads incorporating electrodes implemented in accordance with the present invention may be used with a subcutaneous cardiac monitoring and/or stimulation device. One such device is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In another implementation, one or more noise canceling leads incorporating electrodes may be located in direct contact with the heart, great vessel or coronary vasculature, such as via one or more leads implanted by use of conventional transvenous delivery approaches. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

Certain configurations illustrated herein are generally described as capable of implementing various functions traditionally performed by an implantable cardioverter/defibrillator (ICD), and may operate in numerous cardioversion/defibrillation modes as are known in the art. Exemplary ICD circuitry, structures and functionality, aspects of which can be incorporated in an ITCS device of a type that may benefit from noise canceling electrode configurations, are disclosed in commonly owned U.S. Pat. Nos. 5,133,353; 5,179,945; 5,314,459; 5,318,597; 5,620,466; and 5,662,688, which are hereby incorporated herein by reference in their respective entireties.

In particular configurations, systems and methods can perform functions traditionally performed by pacemakers, such as providing various pacing therapies as are known in the art, in addition to cardioversion/defibrillation therapies. Exemplary pacemaker circuitry, structures and functionality, aspects of which can be incorporated in an ITCS device of a type that may benefit from noise canceling electrode configurations, are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference in their respective entireties. It is understood that ITCS device configurations can provide for non-physiologic pacing support in addition to, or to the exclusion of, bradycardia and/or anti-tachycardia pacing therapies.

An ITCS device in accordance with the present invention can implement diagnostic and/or monitoring functions as well as provide cardiac stimulation therapy. Exemplary cardiac monitoring circuitry, structures and functionality, aspects of which can be incorporated in an ITCS device of a type that may benefit from noise canceling electrode configurations, are disclosed in commonly owned U.S. Pat. Nos. 5,313,953; 5,388,578; and 5,411,031, which are hereby incorporated herein by reference in their respective entireties.

An ITCS device may be used to implement various diagnostic functions, which may involve performing rate-based, pattern and rate-based, and/or morphological tachyarrhythmia discrimination analyses. Subcutaneous, cutaneous, and/or external sensors can be employed to acquire physiologic and non-physiologic information for purposes of enhancing tachyarrhythmia detection and termination. It is understood that configurations, features, and combination of features described in the instant disclosure can be implemented in a wide range of implantable medical devices, and that such embodiments and features are not limited to the particular devices described herein.

Figure 1B:
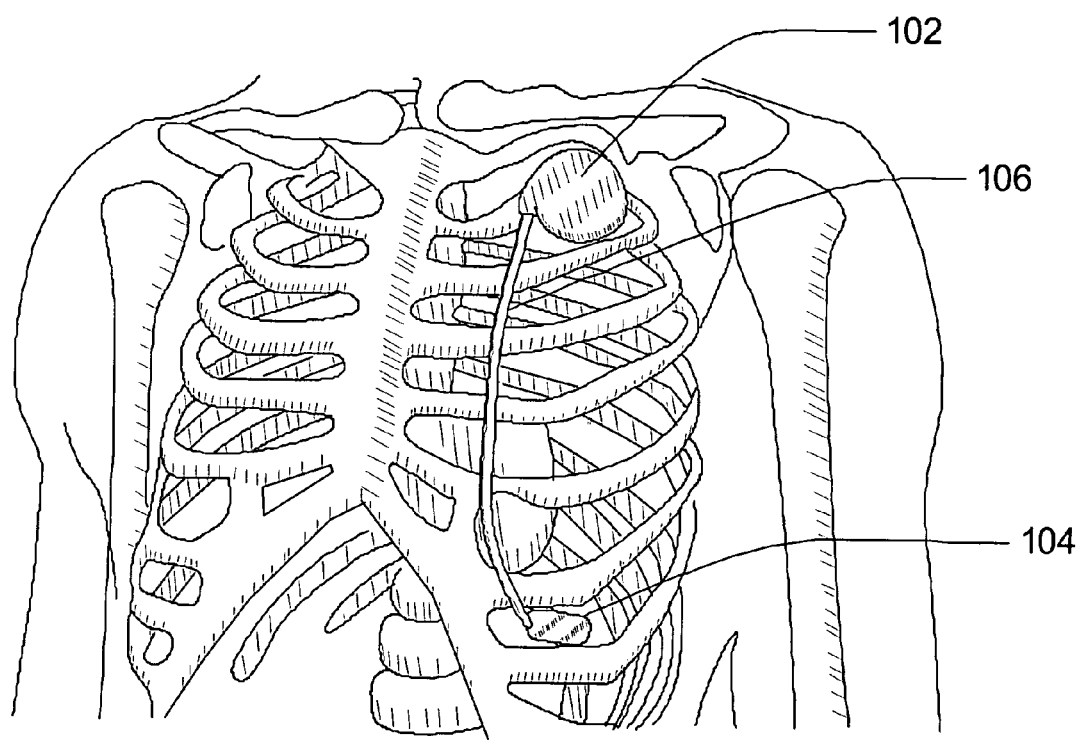

Referring now to FIGS. 1A and 1B of the drawings, there is shown a configuration of an implantable transthoracic cardiac sensing and/or stimulation (ITCS) device having components implanted in the chest region of a patient at different locations. In the particular configuration shown in FIGS. 1A and 1B, the ITCS device includes a housing 102 within which various cardiac sensing, detection, processing, and energy delivery circuitry can be housed. It is understood that the components and functionality depicted in the figures and described herein can be implemented in hardware, software, or a combination of hardware and software. It is further understood that the components and functionality depicted as separate or discrete blocks/elements in the figures can be implemented in combination with other components and functionality, and that the depiction of such components and functionality in individual or integral form is for purposes of clarity of explanation, and not of limitation.

Communications circuitry is disposed within the housing 102 for facilitating communication between the ITCS device and an external communication device, such as a portable or bed-side communication station, patient-carried/worn communication station, or external programmer, for example. The communications circuitry can also facilitate unidirectional or bidirectional communication with one or more external, cutaneous, or subcutaneous physiologic or non-physiologic sensors. The housing 102 is typically configured to include one or more electrodes (e.g., can electrode and/or indifferent electrode). Although the housing 102 is typically configured as an active can, it is appreciated that a non-active can configuration may be implemented, in which case at least two electrodes spaced apart from the housing 102 are employed.

In the configuration shown in FIGS. 1A and 1B, a subcutaneous electrode or electrodes 104 can be positioned under the skin in the chest region and situated distal from the housing 102. The subcutaneous and, if applicable, housing electrode(s) can be positioned about the heart at various locations and orientations, such as at various anterior and/or posterior locations relative to the heart. The subcutaneous electrodes 104 are coupled to circuitry within the housing 102 via a lead assembly 106. One or more conductors (e.g., coils or cables) are provided within the lead assembly 106 and electrically couple the subcutaneous electrode 104 with circuitry in the housing 102. One or more sense, sense/pace or defibrillation electrodes can be situated on the elongated structure of the electrode support, the housing 102, and/or the distal electrode assembly (shown as subcutaneous electrode 104 in the configuration shown in FIGS. 1A and 1B).

In one configuration, the lead assembly 106 is generally flexible and has a construction similar to conventional implantable, medical electrical leads (e.g., defibrillation leads or combined defibrillation/pacing leads). In another configuration, the lead assembly 106 is constructed to be somewhat flexible, yet has an elastic, spring, or mechanical memory that retains a desired configuration after being shaped or manipulated by a clinician. For example, the lead assembly 106 can incorporate a gooseneck or braid system that can be distorted under manual force to take on a desired shape. In this manner, the lead assembly 106 can be shape-fit to accommodate the unique anatomical configuration of a given patient, and generally retains a customized shape after implantation. Shaping of the lead assembly 106 according to this configuration can occur prior to, and during, ITCS device implantation.

In accordance with a further configuration, the lead assembly 106 includes a rigid electrode support assembly, such as a rigid elongated structure that positionally stabilizes the subcutaneous electrode 104 with respect to the housing 102. In this configuration, the rigidity of the elongated structure maintains a desired spacing between the subcutaneous electrode 104 and the housing 102, and a desired orientation of the subcutaneous electrode 104/housing 102 relative to the patient's heart. The elongated structure can be formed from a structural plastic, composite or metallic material, and comprises, or is covered by, a biocompatible material. Appropriate electrical isolation between the housing 102 and subcutaneous electrode 104 is provided in cases where the elongated structure is formed from an electrically conductive material, such as metal.

In one configuration, the rigid electrode support assembly and the housing 102 define a unitary structure (e.g., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure can have an arcuate or angled shape, for example.

According to another configuration, the rigid electrode support assembly defines a physically separable unit relative to the housing 102. The rigid electrode support assembly includes mechanical and electrical couplings that facilitate mating engagement with corresponding mechanical and electrical couplings of the housing 102. For example, a header block arrangement can be configured to include both electrical and mechanical couplings that provide for mechanical and electrical connections between the rigid electrode support assembly and housing 102. The header block arrangement can be provided on the housing 102 or the rigid electrode support assembly. Alternatively, a mechanical/electrical coupler can be used to establish mechanical and electrical connections between the rigid electrode support assembly and housing 102. In such a configuration, a variety of different electrode support assemblies of varying shapes, sizes, and electrode configurations can be made available for physically and electrically connecting to a standard ITCS device housing 102.

It is noted that the electrodes and the lead assembly 106 can be configured to assume a variety of shapes. For example, the lead assembly 106 can have a wedge, chevron, flattened oval, or a ribbon shape, and the subcutaneous electrode 104 can comprise a number of spaced electrodes, such as an array or band of electrodes. Moreover, two or more subcutaneous electrodes 104 can be mounted to multiple electrode support assemblies 106 to achieve a desired spaced relationship amongst subcutaneous electrodes 104.

An ITCS device can incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243, which are hereby incorporated herein by reference in their respective entireties.

Depending on the configuration of a particular ITCS device, a delivery system can advantageously be used to facilitate proper placement and orientation of the ITCS device housing and subcutaneous electrode(s). According to one configuration of such a delivery system, a long metal rod similar to conventional trocars can be used to perform small diameter blunt tissue dissection of the subdermal layers. This tool may be pre-formed straight or curved to facilitate placement of the subcutaneous electrode, or it may be flexible enough to allow the physician to shape it appropriately for a given patient. Exemplary delivery tools, aspects of which can be incorporated into an ITCS device delivery tool, are disclosed in commonly owned U.S. Pat. No. 5,300,106; U.S. patent application No. 10/625,833, filed Jul. 23, 2003; and U.S. Patent Publication No. 2004/0204734; which are hereby incorporated herein by reference.

Figure 1C:
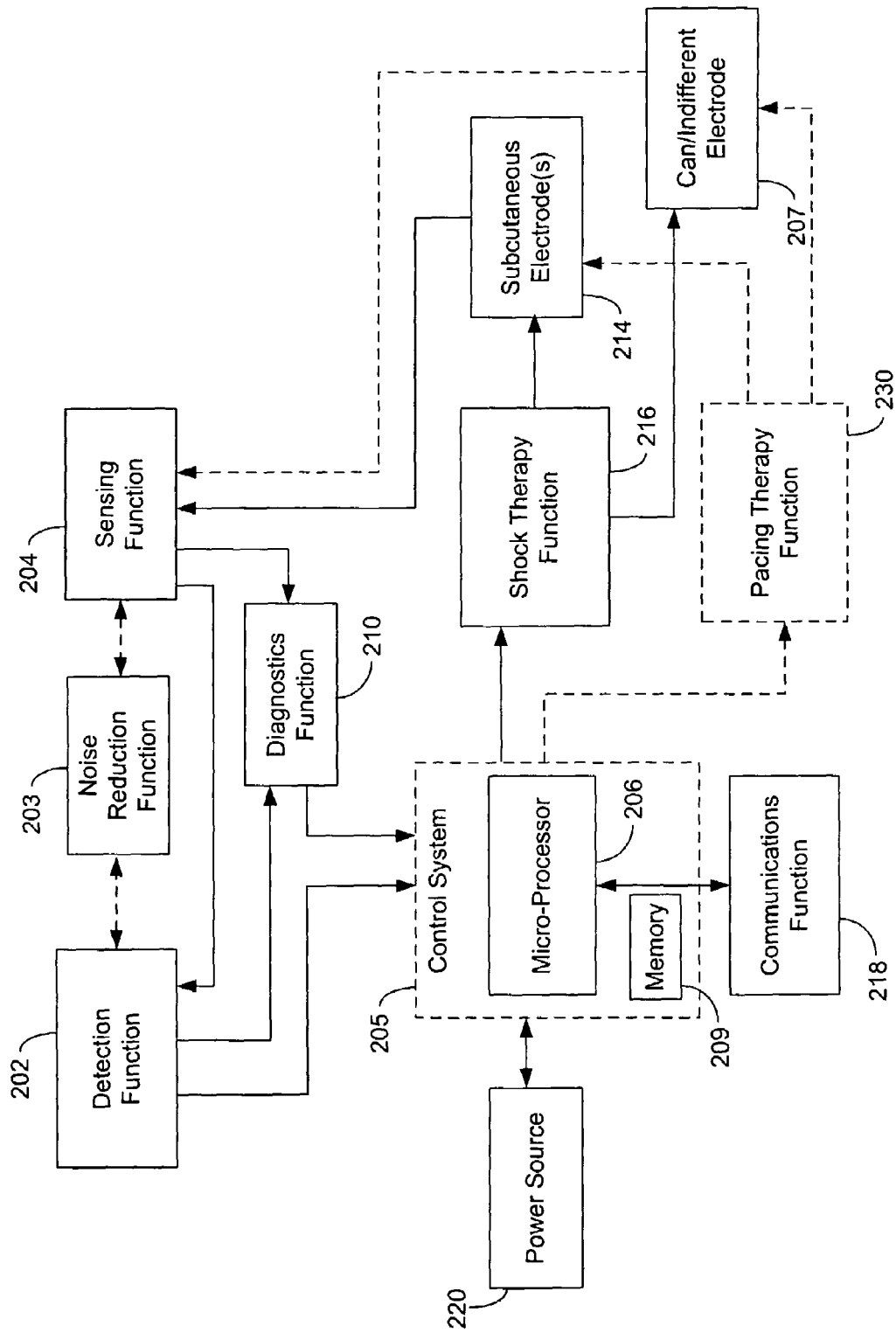
FIG. 1C is a block diagram showing various components of a transthoracic cardiac sensing and/or stimulation device in accordance with an embodiment of the present invention.

FIG. 1C is a block diagram depicting various components of an ITCS device in accordance with one configuration. According to this configuration, the ITCS device incorporates a processor-based control system 205 which includes a micro-processor 206 coupled to appropriate memory (volatile and non-volatile) 209, it being understood that any logic-based control architecture can be used. The control system 205 is coupled to circuitry and components to sense, detect, and analyze electrical signals produced by the heart and deliver electrical stimulation energy to the heart under predetermined conditions to treat cardiac arrhythmias. In certain configurations, the control system 205 and associated components also provide pacing therapy to the heart. The electrical energy delivered by the ITCS device may be in the form of low energy pacing pulses or high-energy pulses for cardioversion or defibrillation.

Cardiac signals are sensed using the subcutaneous electrode(s) 214 and the can or indifferent electrode 207 provided on the ITCS device housing. Cardiac signals can also be sensed using only the subcutaneous electrodes 214, such as in a non-active can configuration. As such, unipolar, bipolar, or combined unipolar/bipolar electrode configurations as well as multi-element noise canceling electrodes and combinations of noise canceling and standard electrodes may be employed. The sensed cardiac signals are received by a sensing block 204, which includes sense amplification circuitry, hardware, firmware, and/or software, and may also include filtering circuitry, hardware, firmware, and/or software, and an analog-to-digital (A/D) converter. The sensed cardiac signals processed by the sensing block 204 may be received by noise reduction block 203, which can further reduce noise before signals are sent to the detection block 202.

Noise reduction block 203 may also be incorporated after detection block 202 in cases where high power or computationally intensive noise reduction algorithms are required. Noise reduction block 203 may also cooperate with or replace the sensing block 204 in cases where noise canceling leads or electrode combinations are to be used in accordance with the present invention. The noise reduction block 203, by way of amplifiers used to perform operations with the electrode signals, may also perform the function of the sensing block 204. Combining the functions of sensing block 204 and noise reduction block 203 may be useful to minimize the necessary componentry and lower the power requirements of the system.

In the illustrative configuration shown in FIG. 1C, the detection block 202 is coupled to, or otherwise incorporates, noise reduction block 203. The noise reduction block 203 operates to improve the SNR of sensed cardiac signals by removing noise content of the sensed cardiac signals introduced from various sources. Typical types of transthoracic cardiac signal noise includes electrical noise and noise produced from skeletal muscles, for example. A number of methodologies for improving the SNR of sensed cardiac signals in the presence of skeletal muscular induced noise, including signal separation techniques incorporating combinations of electrodes and noise canceling multi-element electrodes, are described hereinbelow.

Detection block 202 typically includes a signal processor that coordinates analysis of the sensed cardiac signals and/or other sensor inputs to detect cardiac arrhythmias, such as, in particular, tachyarrhythmia. Rate based and/or morphological discrimination algorithms can be implemented by the signal processor of the detection block 202 to detect and verify the presence and severity of an arrhythmic episode. Exemplary arrhythmia detection and discrimination circuitry, structures, and techniques, aspects of which can be implemented by an ITCS device of a type that may benefit from noise canceling electrode configurations, are disclosed in commonly owned U.S. Pat. Nos. 5,301,677 and 6,438,410, which are hereby incorporated herein by reference in their respective entireties. Arrhythmia detection methodologies particularly well suited for implementation in subcutaneous cardiac monitoring and/or stimulation systems are described hereinbelow.

The detection block 202 communicates cardiac signal information to the control system 205. Memory block 209 of the control system 205 contains parameters for operating in various sensing, defibrillation, and, if applicable, pacing modes, and stores data indicative of cardiac signals received by the detection block 202. The memory block 209 can also be configured to store historical ECG and therapy data, which may be used for various purposes and transmitted to an external receiving device as needed or desired.

In certain configurations, the ITCS device can include diagnostics block 210. The diagnostics block 210 typically receives input signals from the detection block 202 and the sensing block 204. The diagnostics block 210 provides diagnostics data to the control system 205, it being understood that the control system 205 can incorporate all or part of the diagnostics block 210 or its functionality. The control system 205 may store and use information provided by the diagnostics block 210 for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

According to a configuration that provides cardioversion and defibrillation therapies, the control system 205 processes cardiac signal data received from the detection block 202 and initiates appropriate tachyarrhythmia therapies to terminate cardiac arrhythmic episodes and return the heart to normal sinus rhythm. The control system 205 is coupled to shock therapy block 216. The shock therapy block 216 is coupled to the subcutaneous electrode(s) 214 and the can or indifferent electrode 207 of the ITCS device housing. Upon command, the shock therapy block 216 delivers cardioversion and defibrillation stimulation energy to the heart in accordance with a selected cardioversion or defibrillation therapy. In a less sophisticated configuration, the shock therapy block 216 is controlled to deliver defibrillation therapies, in contrast to a configuration that provides for delivery of both cardioversion and defibrillation therapies. Exemplary ICD high energy delivery circuitry, structures and functionality, aspects of which can be incorporated in an ITCS device of a type that may benefit from noise canceling electrode configurations, are disclosed in commonly owned U.S. Pat. Nos. 5,372,606; 5,411,525; 5,468,254; and 5,634,938, which are hereby incorporated herein by reference in their respective entireties.

In accordance with another configuration, an ITCS device can incorporate a cardiac pacing capability in addition to cardioversion and/or defibrillation capabilities. As is shown in dotted lines in FIG. 1C, the ITCS device can include pacing therapy block 230 which is coupled to the control system 205 and the subcutaneous and can/indifferent electrodes 214, 207. Upon command, the pacing therapy block delivers pacing pulses to the heart in accordance with a selected pacing therapy. Control signals, developed in accordance with a pacing regimen by pacemaker circuitry within the control system 205, are initiated and transmitted to the pacing therapy block 230 where pacing pulses are generated. A pacing regimen may be modified by the control system 205.

A number of cardiac pacing therapies may be useful in a transthoracic cardiac monitoring and/or stimulation device. Such cardiac pacing therapies can be delivered via the pacing therapy block 230 as shown in FIG. 1C. Alternatively, cardiac pacing therapies can be delivered via the shock therapy block 216, which effectively obviates the need for separate pacemaker circuitry.

The ITCS device shown in FIG. 1C can be configured to receive signals from one or more physiologic and/or non-physiologic sensors. Depending on the type of sensor employed, signals generated by the sensors can be communicated to transducer circuitry coupled directly to the detection block 202 or indirectly via the sensing block 204. It is noted that certain sensors can transmit sense data to the control system 205 without processing by the detection block 202.

Communications block 218 is coupled to the microprocessor 206 of the control system 205. The communications block 218 allows the ITCS device to communicate with one or more receiving devices or systems situated external to the ITCS device. By way of example, the ITCS device can communicate with a patient-worn, portable or bedside communication system via the communications block 218. In one configuration, one or more physiologic or non-physiologic sensors (subcutaneous, cutaneous, or external of patient) can be equipped with a short-range wireless communication interface, such as an interface conforming to a known communications standard, such as Bluetooth or IEEE 802 standards. Data acquired by such sensors can be communicated to the ITCS device via the communications block 218. It is noted that physiologic or non-physiologic sensors equipped with wireless transmitters or transceivers can communicate with a receiving system external of the patient.

The communications block 218 can allow the ITCS device to communicate with an external programmer. In one configuration, the communications block 218 and the programmer unit (not shown) use a wire loop antenna and a radio frequency telemetric link, as is known in the art, to receive and transmit signals and data between the programmer unit and communications block 218. In this manner, programming commands and data are transferred between the ITCS device and the programmer unit during and after implant. Using a programmer, a physician is able to set or modify various parameters used by the ITCS device. For example, a physician can set or modify parameters affecting sensing, detection, pacing, and defibrillation functions of the ITCS device, including pacing and cardioversion/defibrillation therapy modes.

Typically, the ITCS device is encased and hermetically sealed in a housing suitable for implanting in a human body as is known in the art. Power to the ITCS device is supplied by an electrochemical power source 220 housed within the ITCS device. In one configuration, the power source 220 includes a rechargeable battery. According to this configuration, charging circuitry is coupled to the power source 220 to facilitate repeated non-invasive charging of the power source 220. The communications block 218, or separate receiver circuitry, is configured to receive RF energy transmitted by an external RF energy transmitter. The ITCS device may, in addition to a rechargeable power source, include a non-rechargeable battery. It is understood that a rechargeable power source need not be used, in which case a long-life non-rechargeable battery is employed.

Figure 1D:
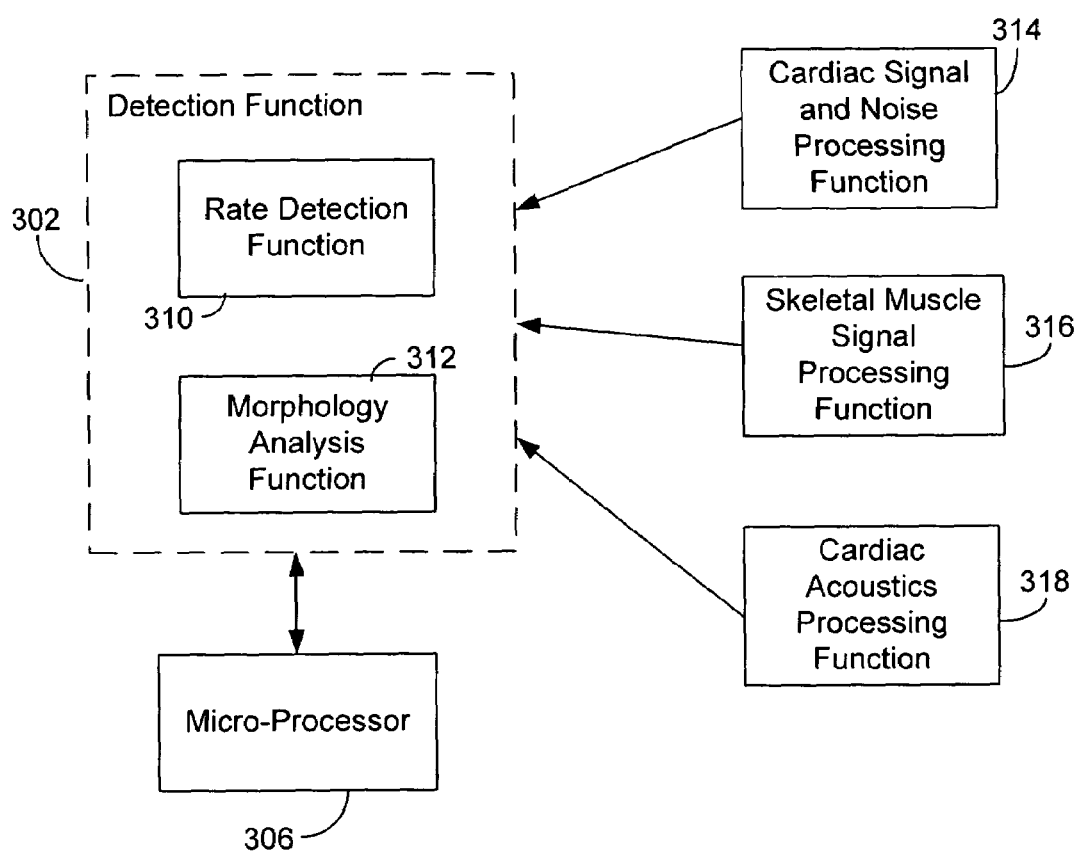
FIG. 1D is a block diagram illustrating various processing and detection components of a transthoracic cardiac sensing and/or stimulation device in accordance with an embodiment of the present invention.

FIG. 1D illustrates a configuration of detection block 302 of an ITCS device, which includes one or both of rate detection block 310 and morphological analysis block 312. Detection and verification of arrhythmias can be accomplished using rate-based discrimination algorithms as known in the art implemented by the rate detection block 310. Arrhythmic episodes can also be detected and verified by morphology-based analysis of sensed cardiac signals as is known in the art. Tiered or parallel arrhythmia discrimination algorithms can also be implemented using both rate-based and morphologic-based approaches. Further, a rate and pattern-based arrhythmia detection and discrimination approach may be employed to detect and/or verify arrhythmic episodes, such as the approach disclosed in U.S. Pat. Nos. 6,487,443; 6,259,947; 6,141,581; 5,855,593; and 5,545,186, which are hereby incorporated herein by reference in their respective entireties.

The detection block 302, which is coupled to a microprocessor 306, can be configured to incorporate, or communicate with, specialized circuitry for processing sensed cardiac signals in manners particularly useful in a transthoracic cardiac sensing and/or stimulation device. As is shown by way of example in FIG. 1D, the detection block 302 can receive information from multiple physiologic and non-physiologic sensors. As illustrated, transthoracic acoustics can be monitored using an appropriate acoustic sensor. Heart sounds, for example, can be detected and processed by cardiac acoustic processing block 318 for a variety of purposes. The acoustics data is transmitted to the detection block 302, via a hardwire or wireless link, and used to enhance cardiac signal detection. For example, acoustics can be used to discriminate normal cardiac sinus rhythm with electrical noise from potentially lethal arrhythmias, such as ventricular tachycardia or ventricular fibrillation.

The detection block 302 can also receive information from one or more sensors that monitor skeletal muscle activity. In addition to cardiac activity signals, skeletal muscle signals are readily detected by transthoracic electrodes. Such skeletal muscle signals can be used to determine the activity level of the patient. In the context of cardiac signal detection, such skeletal muscle signals are considered artifacts of the cardiac activity signal, which can be viewed as noise. Processing block 316 receives signals from one or more skeletal muscle sensors, and transmits processed skeletal muscle signal data to the detection block 302. This data can be used to discriminate normal cardiac sinus rhythm with skeletal muscle noise from cardiac arrhythmias.

As was previously discussed, the detection block 302 is coupled to, or otherwise incorporates, noise-processing block 314. The noise processing block 314 processes sensed cardiac signals to improve the SNR of sensed cardiac signals by reducing noise content of the sensed cardiac signals.

The components, functionality, and structural configurations depicted in FIGS. 1A-1D are intended to provide an understanding of various features and combination of features that can be incorporated in an ITCS device. It is understood that a wide variety of ITCS and other implantable cardiac monitoring and/or stimulation device configurations are contemplated, ranging from relatively sophisticated to relatively simple designs. As such, particular ITCS or cardiac monitoring and/or stimulation device configurations can include particular features as described herein, while other such device configurations can exclude particular features described herein.

In accordance with embodiments of the invention, an ITCS device can be implemented to include a subcutaneous electrode system that provides for cardiac sensing and arrhythmia therapy delivery. According to one approach, an ITCS device may be implemented as a chronically implantable system that performs monitoring, diagnostic and/or therapeutic functions. The ITCS device may automatically detect and treat cardiac arrhythmias. In one configuration, the ITCS device includes a pulse generator and one or more electrodes that are implanted subcutaneously in the chest region of the body, such as in the anterior thoracic region of the body. The ITCS device can be used to provide atrial and ventricular therapy for bradycardia and tachycardia arrhythmias. Tachyarrhythmia therapy can include cardioversion, defibrillation and anti-tachycardia pacing (ATP), for example, to treat atrial or ventricular tachycardia or fibrillation. Bradycardia therapy can include temporary post-shock pacing for bradycardia or asystole. Methods and systems for implementing post-shock pacing for bradycardia or asystole are described in commonly owned U.S. Pat. No. 7,392,081, which is incorporated herein by reference in its entirety.

In one configuration, an ITCS device according to one approach can utilize conventional pulse generator and subcutaneous electrode implant techniques. The pulse generator device and electrodes may be chronically implanted subcutaneously. Such an ITCS can be used to automatically detect and treat arrhythmias similarly to conventional implantable systems. In another configuration, the ITCS device may comprise a unitary structure (e.g., a single housing/unit). The electronic components and electrode conductors/connectors are disposed within or on the unitary ITCS device housing/electrode support assembly.

The ITCS device contains the electronics and can be similar to a conventional implantable defibrillator. High voltage shock therapy can be delivered between two or more electrodes, one of which may be the pulse generator housing (e.g., can), placed subcutaneously in the thoracic region of the body.

Additionally or alternatively, the ITCS device may also provide lower energy electrical stimulation for bradycardia therapy. The ITCS device may provide brady pacing similarly to a conventional pacemaker. The ITCS device may provide temporary post-shock pacing for bradycardia or asystole. Sensing and/or pacing can be accomplished using sense/pace electrodes positioned on an electrode subsystem also incorporating shock electrodes, or by separate electrodes implanted subcutaneously.

The ITCS device may detect a variety of physiological signals that may be used in connection with various diagnostic, therapeutic or monitoring implementations. For example, the ITCS device may include sensors or circuitry for detecting respiratory system signals, cardiac system signals, and signals related to patient activity. In one embodiment, the ITCS device senses intrathoracic impedance, from which various respiratory parameters may be derived, including, for example, respiratory tidal volume and minute ventilation. Sensors and associated circuitry may be incorporated in connection with an ITCS device for detecting one or more body movement or body position related signals. For example, accelerometers and GPS devices may be employed to detect patient activity, patient location, body orientation, or torso position.

The ITCS device may be used within the structure of an advanced patient management (APM) system. Advanced patient management systems may allow physicians to remotely and automatically monitor cardiac and respiratory functions, as well as other patient conditions. In one example, implantable cardiac rhythm management systems, such as cardiac pacemakers, defibrillators, and resynchronization devices, may be equipped with various telecommunications and information technologies that enable real-time data collection, diagnosis, and treatment of the patient.

An ITCS device according to one approach provides an easy to implant therapeutic, diagnostic or monitoring system. The ITCS system can be implanted without the need for intravenous or intrathoracic access, providing a simpler, less invasive implant procedure and minimizing lead and surgical complications. In addition, this system would have advantages for use in patients for whom transvenous lead systems cause complications. Such complications include, but are not limited to, surgical complications, infection, insufficient vessel patency, complications associated with the presence of artificial valves, and limitations in pediatric patients due to patient growth, among others. An ITCS system according to this approach is distinct from conventional approaches in that it is preferably configured to include a combination of two or more electrode subsystems that are implanted subcutaneously in the anterior thorax.

Figure 2:
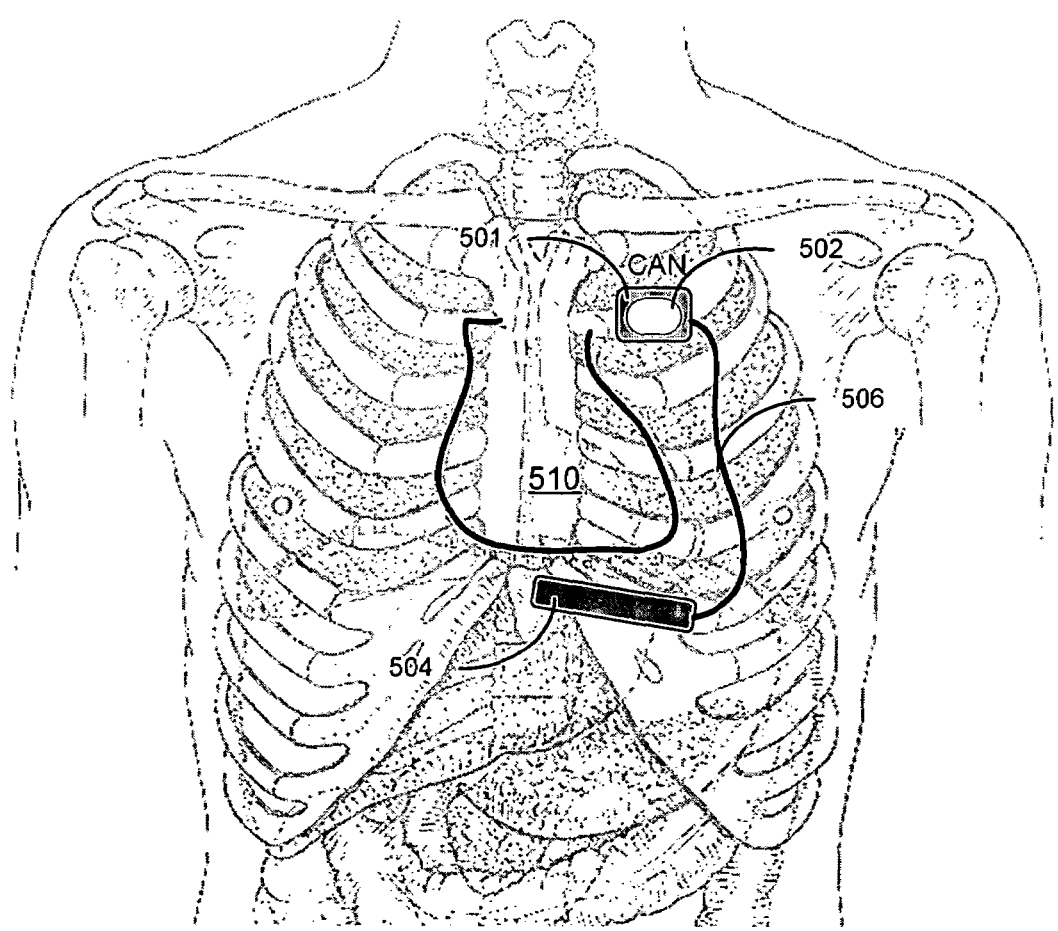
FIG. 2 is a diagram illustrating components of a transthoracic cardiac sensing and/or stimulation device including noise canceling electrodes in accordance with an embodiment of the present invention.

In one configuration, as is illustrated in FIG. 2, electrode subsystems of an ITCS system are arranged about a patient's heart 510. The ITCS system includes a first electrode subsystem, comprising a can electrode 502, and a second electrode subsystem 504 that includes at least one noise canceling electrode and/or a plurality of electrodes useful in a noise canceling configuration. The second electrode subsystem 504 may comprise a number of electrodes used for sensing and/or electrical stimulation. In various configurations, the second electrode subsystem 504 may comprise a single noise canceling electrode or a combination of electrodes. The single noise canceling electrode or combination of electrodes of the second electrode subsystem 504 may include coil electrodes, tip electrodes, ring electrodes, multi-element coils, spiral coils, spiral coils mounted on non-conductive backing, screen patch electrodes, and other electrode configurations as will be described below. A suitable non-conductive backing material is silicone rubber, for example.

The can electrode 502 is positioned on the housing 501 that encloses the ITCS device electronics. In one embodiment, the can electrode 502 comprises the entirety of the external surface of housing 501. In other embodiments, various portions of the housing 501 may be electrically isolated from the can electrode 502 or from tissue. For example, the active area of the can electrode 502 may comprise all or a portion of either of the first and second large surfaces of the housing 501 to direct current flow in a manner advantageous for cardiac sensing and/or stimulation.

In accordance with one embodiment, the housing 501 may resemble that of a conventional implantable ICD, is approximately 20-100 cc in volume, with a thickness of 0.4 to 2 cm and with a surface area on each face of approximately 30 to 100 $cm^2$. As previously discussed, portions of the housing may be electrically isolated from tissue to optimally direct current flow. For example, portions of the housing 501 may be covered with a non-conductive, or otherwise electrically resistive, material to direct current flow. Suitable non-conductive material coatings include those formed from silicone rubber, polyurethane, or parylene, for example.

In addition, or alternatively, all or portions of the housing 501 may be treated to change the electrical conductivity characteristics thereof for purposes of optimally directing current flow. Various known techniques can be employed to modify the surface conductivity characteristics of the housing 501, such as by increasing or decreasing surface conductivity, to optimize current flow. Such techniques can include those that mechanically or chemically alter the surface of the housing 501 to achieve desired electrical conductivity characteristics.

An ITCS device can be implemented to include a noise rejection/reduction capability to improve noise rejection of cardiac signals sensed by subcutaneous electrodes. This noise rejection/reduction approach advantageously reduces the risk of false positives for detection algorithms by improving the signal to noise ratio of the cardiac signal.

According to one approach, a set of primary electrodes and a secondary set of electrodes are employed. The primary electrodes are selected to optimize sensing of cardiac signals while the secondary electrodes are selected in an orientation to attempt to minimize cardiac signal sensing. A linear combination of signals from the primary and secondary electrodes can then be produced in a way so as to minimize non-cardiac signals (e.g., noise) and therefore improve the signal to noise ratio of the cardiac signal. Although sets of primary and secondary electrodes are typically used, it is understood that the primary or secondary electrode set can instead be defined by a single electrode.

An ITCS device can include various pairs of matched electrodes. Every pair of electrodes has a corresponding pair of spatially diverse electrodes. Spatially diverse electrodes can, for example, include sets of electrodes arranged in an orthogonal relationship to one another, it being understood that other non-orthogonal relationships can be employed. For each spatially diverse pair of electrodes, a primary pair of electrodes would be selected based on the largest content of cardiac signal. The corresponding spatially diverse electrodes would then be selected for the purpose of noise reduction.

In one configuration, orthogonal electrode pairs can be placed on orthogonal (x-y, x-z, y-z) planes of one or multiple electrode units, and the cardiac signals from these electrode pairs used to compute the component of the cardiac activation vector along orthogonal planes.

An ITCS device which implements a noise reduction approach consistent with the present invention provides for simplified post processing of cardiac signals in the presence of noise or non-cardiac artifacts since the signal to noise ratio of the signal can be significantly improved.

According to one configuration, a cardiac monitoring and/or stimulation device is configured to include a pulse generator having a controller and a plurality of implantable electrodes coupled to the pulse generator. A first combination of electrodes is adapted to preferentially sense cardiac signals. A second combination of electrodes is adapted to preferentially sense noise signals (e.g., non-cardiac signals). The electrodes can be subcutaneous electrodes arranged in a non-contacting relationship with respect to cardiac tissue and vasculature. The electrodes can alternatively be surface electrodes or conventional transvenous, epicardial, and/or endocardial electrodes or combinations of various types of electrodes.

The first combination of electrodes can be selected by the controller of the pulse generator to preferentially sense the cardiac signals, and the second combination of electrodes can be selected by the controller to preferentially sense the noise signals. For example, the controller can select combinations of the plurality of electrodes, and senses a cardiac signal component and a noise component of signals acquired by each of the controller selected electrode combinations. The controller, for example, can select the first combination of electrodes as an electrode combination that provides a cardiac signal response that exceeds a threshold, and the controller can select the second combination of electrodes as an electrode combination that provides a noise component response.

The controller of the cardiac monitoring and/or stimulation device can, for example, select the first combination of electrodes as an electrode combination that provides a cardiac signal response that exceeds an SNR threshold. The controller can also select the second combination of electrodes as an electrode combination that provides a cardiac signal response substantially lower than the SNR threshold, such as lower than a second SNR threshold, where the second SNR threshold is substantially lower than the SNR threshold associated with sensing the cardiac signal response.

It is contemplated that a useful SNR may not be available for use by the cardiac monitoring and/or stimulation device. For example, signals may have effectively no noise, or there may be noise, but with no measurably significant impact. It may be useful to provide for signal selection based on thresholds independent of SNRs.

In one embodiment independent of SNRs, the controller of the cardiac monitoring and/or stimulation device can, for example, select the first combination of electrodes as an electrode combination that provides a cardiac signal response exceeding a threshold. The controller can also select the second combination of electrodes as an electrode combination that provides a cardiac signal response substantially lower than the threshold, such as lower than a second threshold, where the second threshold is substantially lower than the threshold associated with sensing the cardiac signal response. In another embodiment independent of SNRs, a first set of electrodes may be selected that provides a signal above a first threshold, and a second set of electrodes may be selected where the signal from the electrodes selected is, for example, below a second threshold, or below a percentage of the first threshold.

The physical arrangement of electrodes or electrode elements on a multi-element electrode (such as, for example, an array electrode) may be designed to provide more than one signal, or vector, to the cardiac monitoring and/or stimulation device. A first combination of electrodes can be physically arranged to preferentially sense cardiac signals and a second combination of electrodes can be physically arranged to preferentially sense the noise signals. For example, the first combination of electrodes can be physically arranged to be spatially diverse (e.g., substantially orthogonal) with respect to the second combination of electrodes. In such an arrangement, the first combination of electrodes is preferably arranged to provide a cardiac signal response that exceeds an SNR threshold, and the second combination of electrodes is preferably arranged to provide a cardiac signal response substantially lower than the SNR threshold or lower than a second SNR threshold.

The first and second electrode combinations typically include electrodes positioned about a patient's heart. The first electrode combination can, for example, include at least one electrode from the second electrode combination. The second electrode combination can include at least one electrode from the first electrode combination. Other electrode combinations are possible when defining the first and second electrode combinations. It is noted that one or more electrodes of the second electrode combination can be electrically shielded.

For example, a first and a second electrode of one or both of the first and second electrode combinations can be positioned in an opposing relationship about a patient's heart. Also, each of the electrodes of one or both of the first and second electrode combinations can be positioned adjacent a particular surface of a patient's heart.

The first electrode combination can include n electrodes positioned at a first location relative to a patient's heart and at least n+1 electrodes positioned at a second location relative to the patient's heart, where n is an integer equal to or greater than 1. Further, the second electrode combination can include n electrodes positioned at a first location relative to a patient's heart and at least n+1 electrodes positioned at a second location relative to the patient's heart, where n is an integer equal to or greater than 1.

At least one of the electrodes of the first and second electrode combinations can be provided on a support structure spaced apart from the pulse generator, and at least one of the electrodes of the first and second electrode combinations can be provided at a housing of the pulse generator.

In another configuration, at least one of the electrodes of the first and second electrode combinations is provided on a first support structure spaced apart from the pulse generator, and at least one of the electrodes of the first and second electrode combinations is provided on a second support structure spaced apart from the pulse generator. The first support structure can be configured to present the electrodes as an array of electrodes. In one approach, at least one or more of the electrodes of the first and second electrode combinations are provided in or on a housing of the pulse generator. In another approach, at least two electrodes of each of the first and second electrode combinations are arranged in an orthogonal relationship on a support structure spaced apart from the pulse generator. The support structure can have a circular or elliptical shape, a polygonal shape, a curved or hook shape, or other shape, such as an arrow shape. The support structure can also constitute the tines or other arrangement attached to the lead body for fixation.

The cardiac signals sensed by the first combination of electrodes typically comprise a cardiac signal component and a noise component. The controller can be implemented to cooperate with noise reduction circuitry to reduce the noise component of the cardiac signals using the sensed noise signals. For example, the cardiac signals sensed by the first combination of electrodes can comprise a cardiac signal component and a noise component, and the controller can coordinate the process of linearly combining the sensed cardiac signals with the sensed noise signals to reduce the noise component of the cardiac signals.

In accordance with a scanning methodology, combinations of the plurality of electrodes are selected, and a cardiac signal component and a noise component of signals acquired by each of the selected electrode combinations are sensed. Selecting the first sensing vector can involve selecting a combination of electrodes that provides a cardiac signal response that exceeds a threshold, and selecting the second sensing vector can involve selecting a combination of electrodes that provides a noise component response. For example, selecting the first sensing vector can involve selecting a combination of electrodes that provides a cardiac signal response that exceeds an SNR threshold, and selecting the second sensing vector can involve selecting a combination of electrodes that provides a cardiac signal response substantially lower than the SNR threshold or lower than a second SNR threshold, where the second SNR threshold is substantially lower than that associated with cardiac signal response sensing.

Selecting the first and second sensing vectors involves selecting a first combination of electrodes that is spatially diverse with respect to a second combination of electrodes, the first combination of electrodes providing the first sensing vector and the second combination of electrodes providing the second sensing vector. Selecting the first electrode combination can involve selecting at least one electrode from the second electrode combination, and selecting the second electrode combination can involve selecting at least one electrode from the first electrode combination.

The sensing method can further involve reducing a noise component of cardiac activity signals using the noise signals, such as by linearly combining cardiac activity signals with the noise signals to reduce a noise component of the cardiac activity signals.

FIGS. 3-13 illustrate electrode configurations, sensing vectors, combination of sensing vectors, and waveforms that demonstrate the efficacy of noise cancellation cardiac electrode implementations as described herein. FIGS. 3-11 illustrate various electrode configurations placed about the heart particularly useful for noise cancellation. FIGS. 8-11 illustrate several multi-element electrode configurations that provide for a cardiac sensing/noise cancellation approach that exploits spatial diversity and separation between electrode elements.

Figure 3:
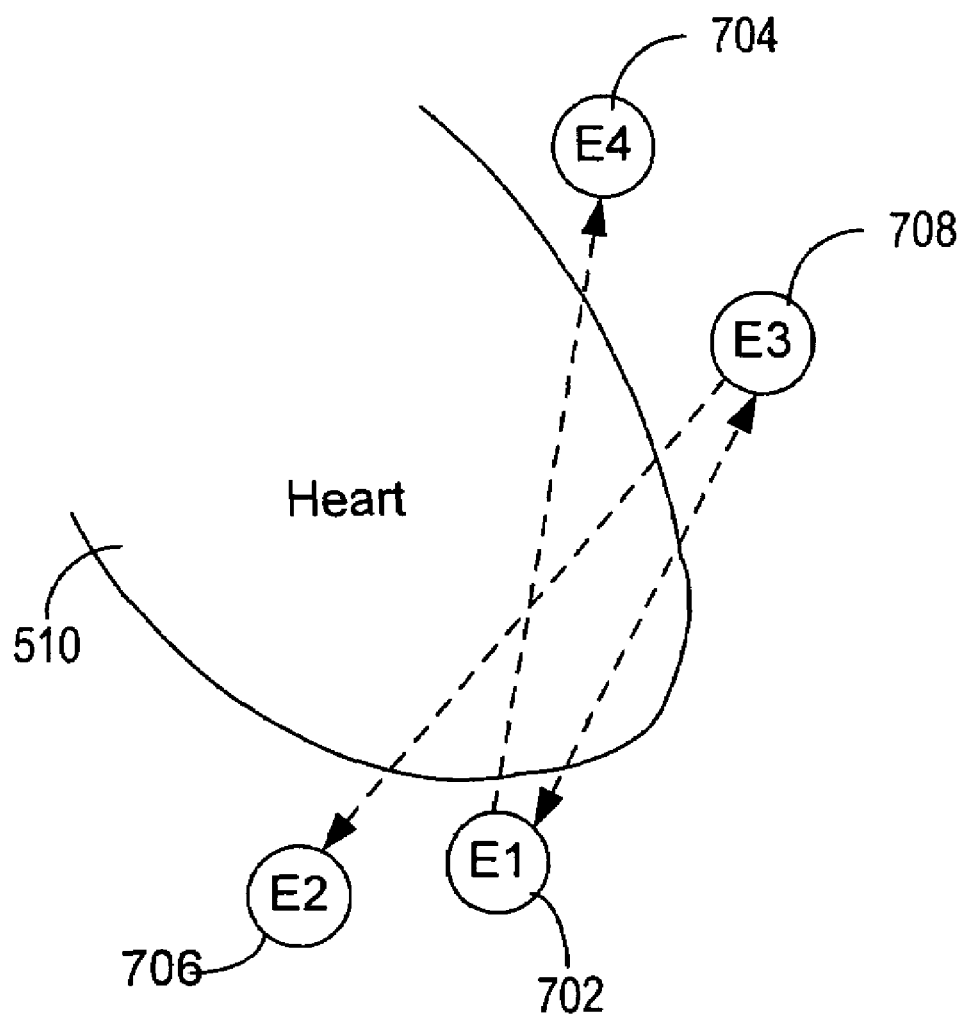
FIG. 3 is an example of an electrode configuration in accordance with the present invention.
Figure 12:
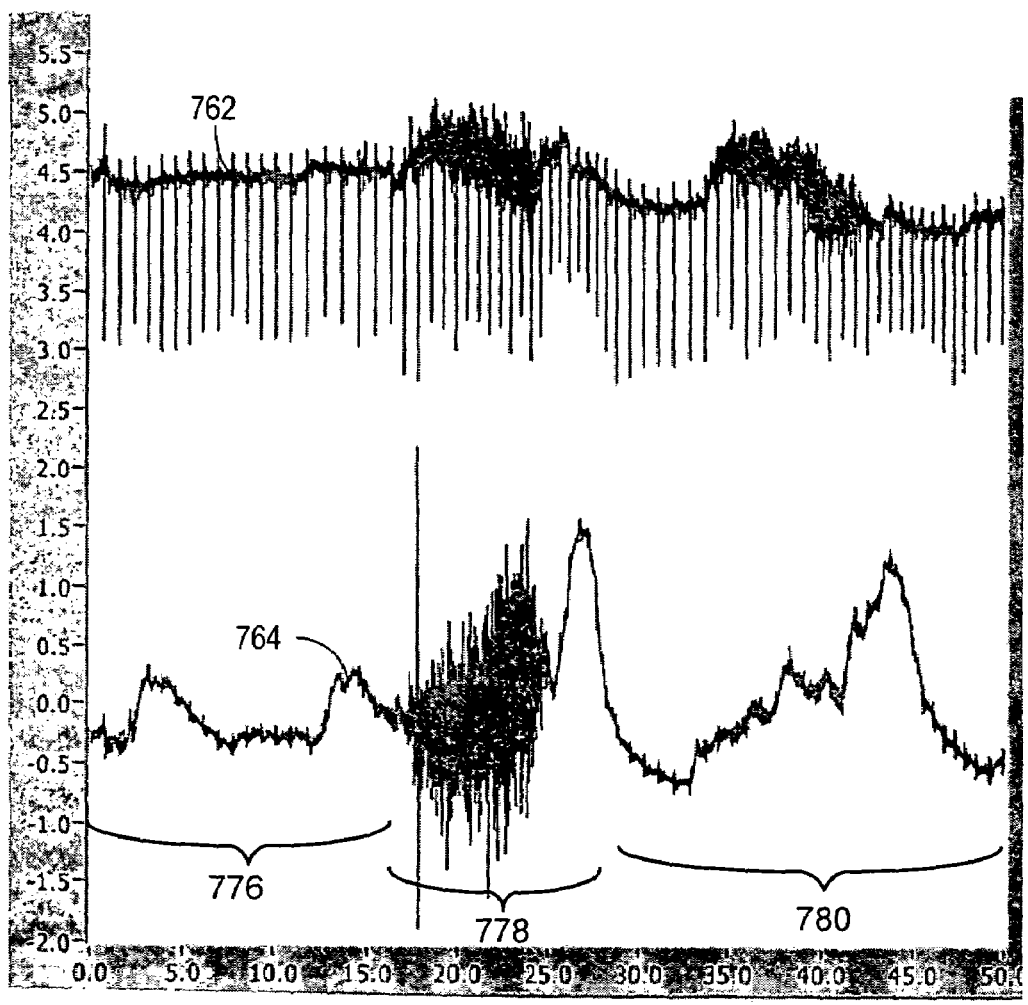
FIG. 12 illustrates signal plots developed using the electrode arrangement of FIG. 6.

FIG. 3 illustrates one configuration of subcutaneous electrodes situated about the heart 510. A first electrode 702 (E1) and a second electrode 706 (E2) are situated adjacent one surface of the heart 510, and a third electrode 708 (E3) and a fourth electrode 704 (E4) are situated adjacent a second surface of the heart 510. The first and second surfaces can be on opposing sides of the heart 510, as is shown in FIG. 3. As can be seen in the sense vector waveforms of FIGS. 12 (note that FIG. 12 shows signals collected from the electrode configuration shown in FIG. 6.) and 13 (further described below), judicious selection of electrode combinations can provide for preferential sensing of cardiac activity and preferential sensing of non-cardiac activity (e.g., skeletal muscular noise and other non-cardiac activity related noise).

Processing of these sense signals, such as by linearly combining the sensed cardiac signals with the sensed noise signals (e.g., subtraction), can be performed to essentially remove the noise component from the cardiac signal, thereby increasing the SNR of the cardiac signal. It is noted that at least some cardiac tissue can be electrically stimulated via energy deliverable by at least some of the electrodes (e.g., E1-E4) or by other electrodes dedicated for energy delivery.

Figure 4A:
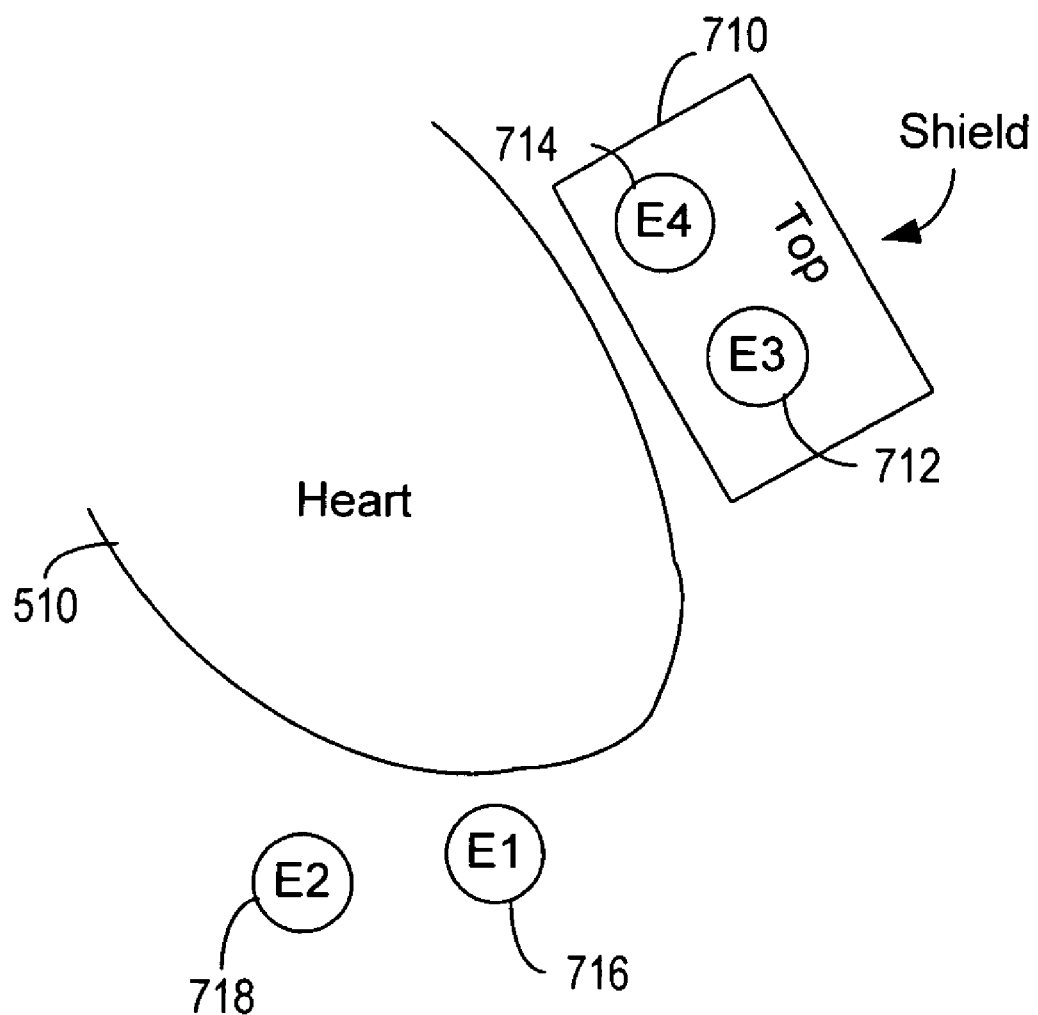

FIGS. 4A, 4B, 4C and 4D illustrate sets of shielded electrodes. In FIG. 4A, an electrode 712 (E3) and an electrode 714 (E4) are shielded from direct heart electrical potentials by a shield 710. Shielded electrodes 712 (E3) and 714 (E4) provide for enhanced sensing of non-cardiac related activity (e.g., noise). An electrode 716 (E1) and an electrode 718 (E2) are not shielded, and have direct electrical paths to the heart. This combination assures that the non-shielded electrodes have a minimum path for direct electrical potential measurement. The shield 710 assures that the shielded electrodes 712 and 714 have a more complex electrical path to the heart and that these electrodes will preferentially sense localized signals.

In FIG. 4B, a bottom view of the shield 710 is illustrated. The bottom of shield 710 is positioned towards the heart 510. An electrode 712' (E3') and an electrode 714' (E4') are shielded from muscle electrical potentials by the shield 710, while optionally the electrode 712 (E3) and the electrode 714 (E4) are located on top of the shield 710 as illustrated in FIG. 4A, and shielded from the direct heart electrical potentials. Electrodes 712' (E3') and 714' (E4') provide for enhanced sensing of cardiac related activity at effectively the same location as shielded electrodes 712 (E3) and 714 (E4) that provide, for example, skeletal muscle dominated signals.

Figure 4C:
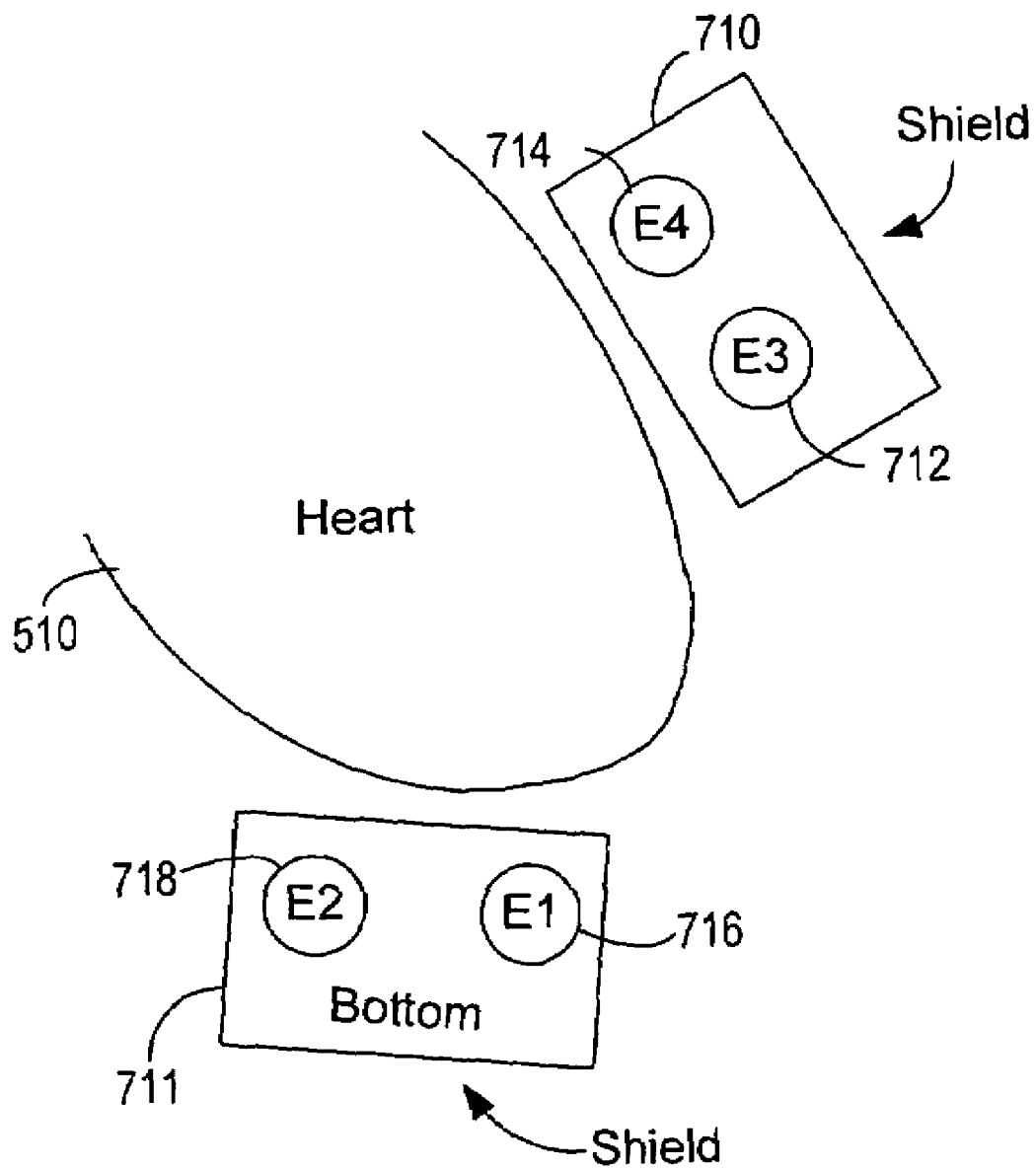

In FIG. 4C, a bottom view of a shield 711 is illustrated. The bottom of shield 711 is positioned towards the heart 510. In the shielded embodiment illustrated in FIG. 4C, the electrode 716 (E1) and the electrode 718 (E2) are shielded from muscle electrical potentials by the shield 711. Although the embodiments illustrated in FIG. 4C are shown with the shield arrangement 710 of FIG. 4A, it should be understood that the shield arrangement 710 illustrated in FIG. 4B, or any other desirable electrode arrangement, is contemplated in combination with the shield arrangements 711 illustrated in FIG. 4C.

Figure 4D:
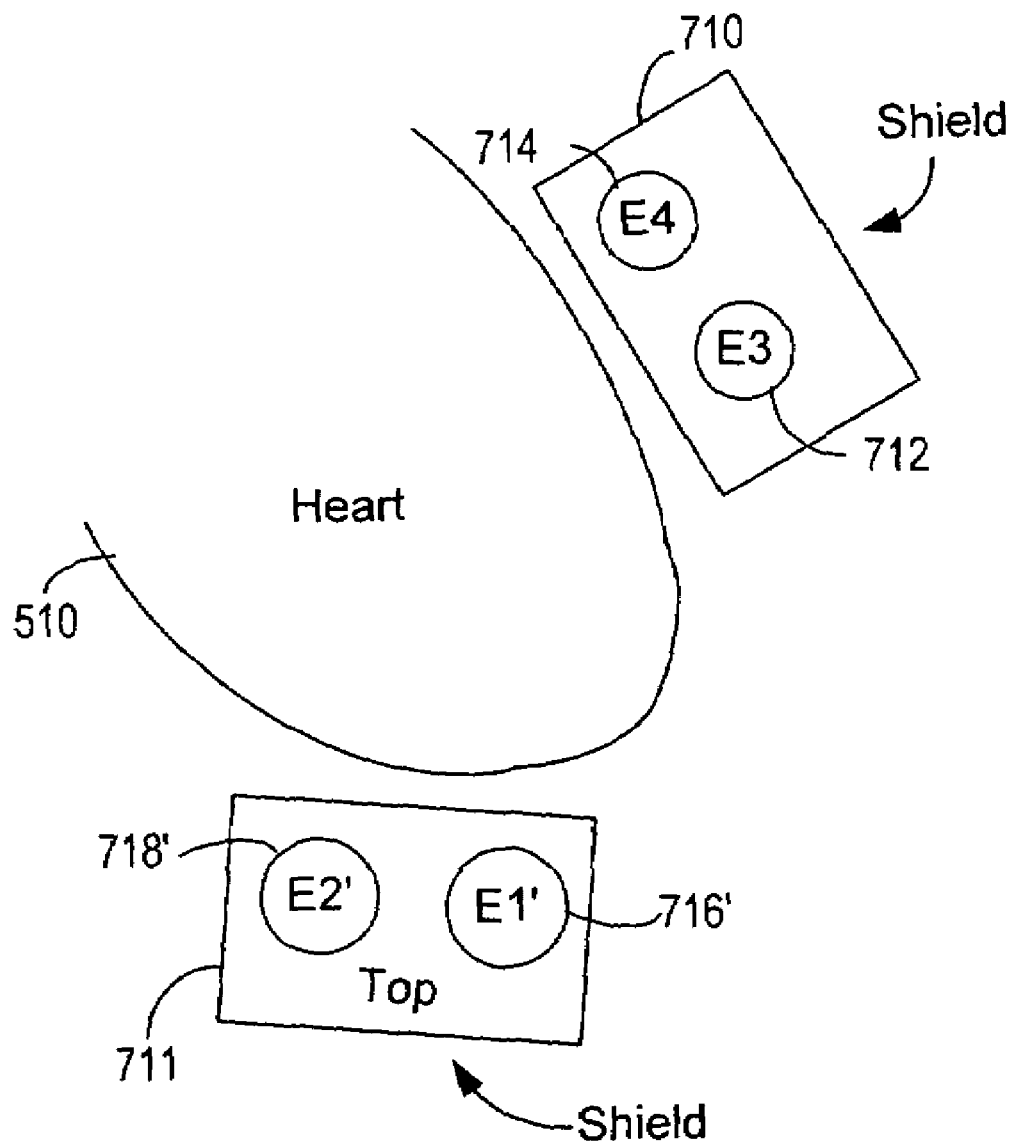

In FIG. 4D, a top view of the shield 711 is illustrated. The top of shield 711 is positioned away the heart 510. An electrode 716' (E1') and an electrode 718' (E2') are shielded from direct heart electrical potentials by the shield 711, while optionally the electrode 716 (E1) and the electrode 718 (E2) (illustrated in FIG. 4C) are located on bottom of the shield 711, and shielded from direct skeletal muscle electrical potentials. Electrodes 716 (E1) and the electrode 718 (E2) may be provided for enhanced sensing of cardiac related activity at effectively the same location as shielded electrode 716' (E1') and electrode 718' (E2') that provide, for example, skeletal muscle dominated signals. Although the embodiments illustrated in FIG. 4D are shown with the shield arrangement 710 of FIG. 4A, it should be understood that the shield arrangement 710 illustrated in FIG. 4B, or any other desirable electrode arrangement, is contemplated in combination with the shield arrangements 711 illustrated in FIG. 4D.

Figure 5:
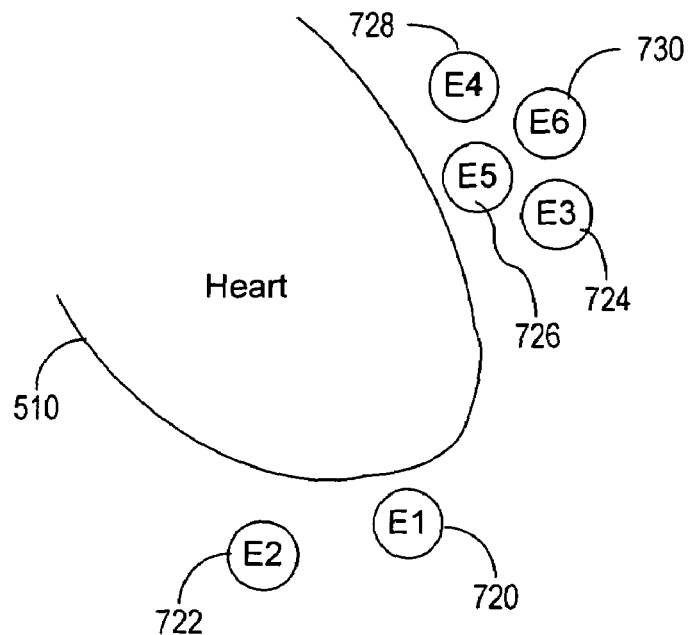
FIG. 5 is another example of a noise canceling electrode configuration in accordance with the present invention.

FIG. 5 illustrates an electrode configuration in which a total of six electrodes, E1-E6, are employed. An electrode 720 (E1) and an electrode 722 (E2) are illustrated inferior to the apex of the heart 510. A set of electrodes including a first electrode 724 (E3) a second electrode 728 (E4) a third electrode 726 (E5) and a fourth electrode 730 (E6) are illustrated positioned left and superior to the apex of the heart 510. The set of electrodes may be four individual electrodes, a four element array electrode, or a four element multi-element electrode, for example. The four electrodes 724, 726, 728, and 730 may be positioned in an orthogonal arrangement to electrically isolate cardiac signals from noise signals.

Figure 6:
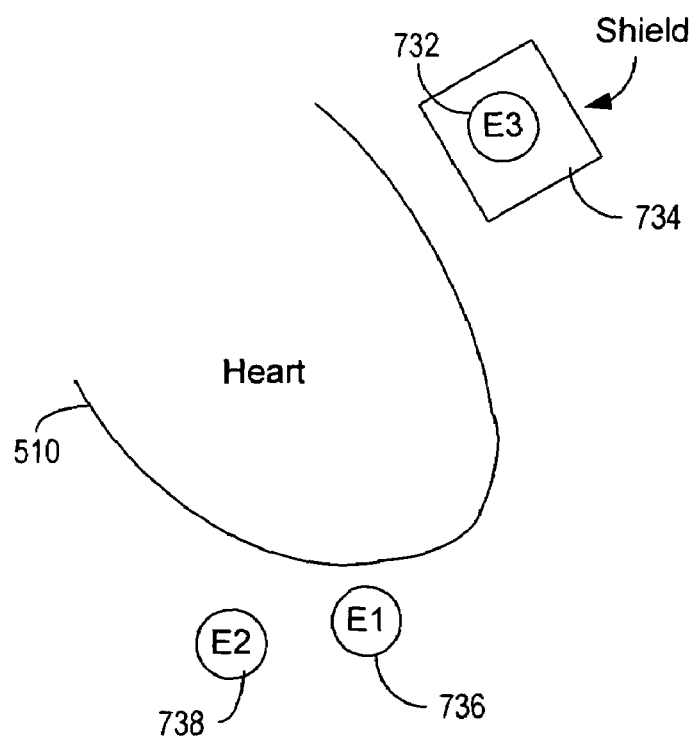
FIG. 6 is another example of a shielded noise canceling electrode configuration in accordance with the present invention.
Figure 7:
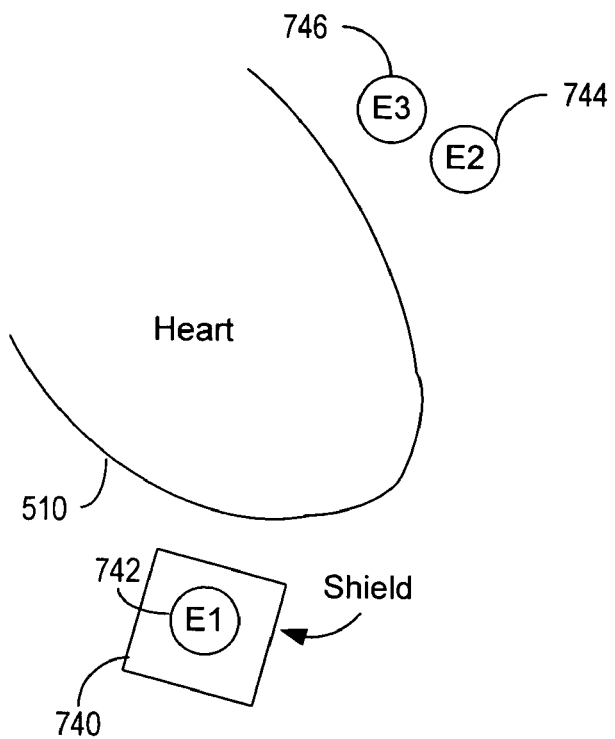
FIG. 7 is yet another example of a shielded noise canceling electrode configuration in accordance with the present invention.

FIG. 6 illustrates another configuration, in which only first electrode 732 (E3) is shielded. An electrode 736 (E1) and an electrode 738 (E2) are not shielded, and have direct electrical paths to the heart. FIG. 7 also illustrates a configuration in which only one electrode, an electrode 742 (E1), is shielded. An electrode 744 (E2) and an electrode 746 (E3) are not shielded. In this configuration, the shielded electrode 742 is located inferior to the apex of the heart 510, and the non-shielded electrodes 744 and 746 are placed left of the atrium of the heart 510.

Figure 8:
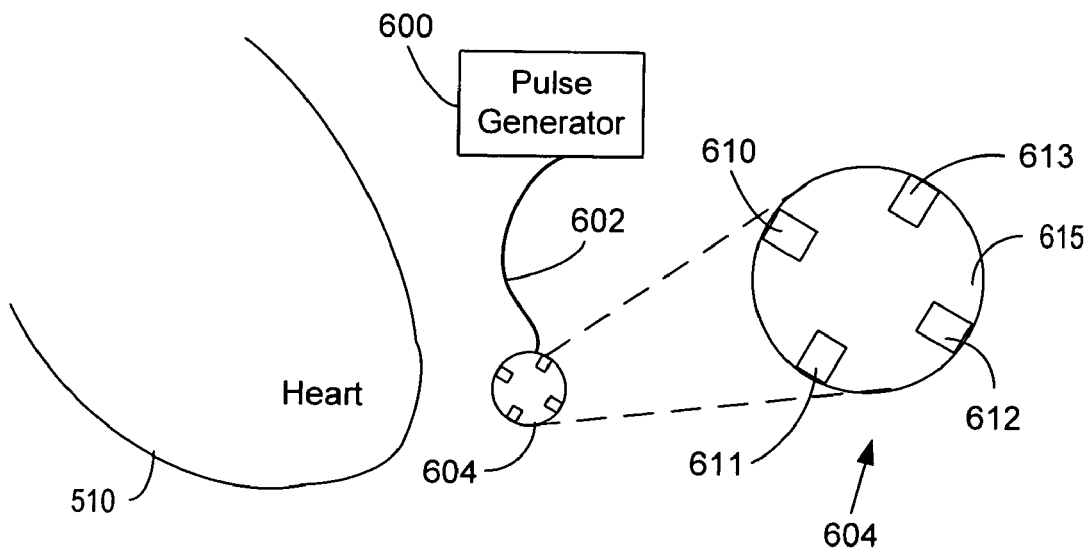
FIG. 8 is a multi-element noise canceling electrode configuration in accordance with the present invention.

FIGS. 8-11 depict several configurations of multi-element subcutaneous electrode systems or arrays by which a noise canceling methodology of the type described herein can be implemented. In FIG. 8, a pulse generator 600 is coupled to a subcutaneous electrode system 604 via a lead 602. The exploded view of the electrode system 604 shows four electrodes 610, 611, 612, 613 positioned in a spatially diverse manner on a support 615. In this particular configuration, the electrodes 610, 611, 612, 613 are positioned in an orthogonal relationship with respect to one another about the support 615.

A first subset of the electrodes 610, 611, 612, 613 can be selected (e.g., via scanning) or specified (e.g., via positioning) as the primary or cardiac signal sensing electrode combination, and a second subset of the electrodes 610, 611, 612, 613 can be selected or specified as the secondary or "noise" sensing electrode combination. For example, electrodes 610 and 612 can form the first electrode combination for preferentially sensing the cardiac signal, and electrodes 611 and 613 can form the second electrode combination for preferentially sensing noise or non-cardiac activity. It is understood that the electrodes provided on the support 615 can be paired or grouped with one or more electrodes provided on the housing of the pulse generator 600 or other electrodes positioned elsewhere to define various primary and/or secondary electrode combinations.

Figure 9:
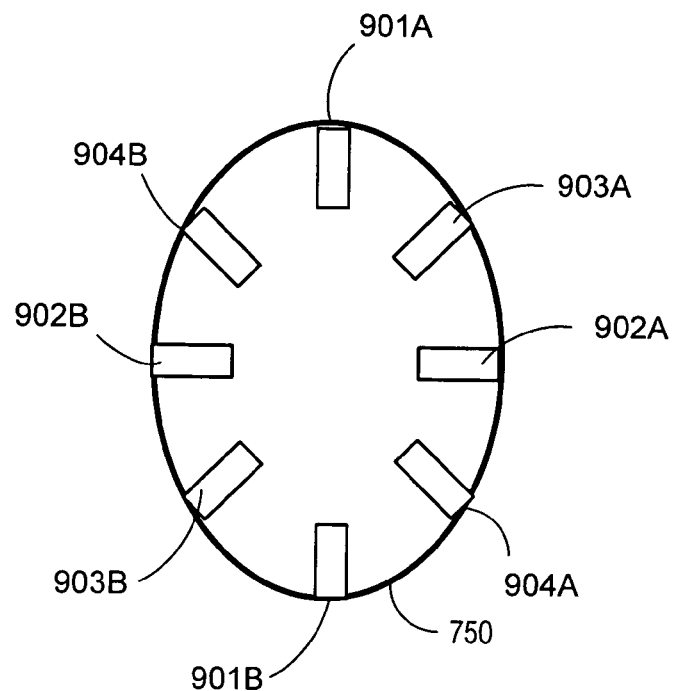
FIG. 9 is another multi-element noise canceling electrode configuration in accordance with the present invention.

FIG. 9 illustrates another configuration of a subcutaneous electrode array that includes eight electrodes 901A-904A and 901B-904B. In this embodiment, pairs or groups (e.g., >2) of electrodes can be selected to define primary and secondary electrode combinations. The increased number of electrodes in the configuration of FIG. 9 in comparison to that of FIG. 8 provides for an increased number of selectable combinations of spatially diverse electrodes for defining cardiac and noise sensing electrode sets. The pulse generator 600 (FIG. 8) may sample electrode combinations to determine optimum electrode combinations for cardiac signal sensing.

For example, and as shown in FIG. 9, electrodes 901A and 901B can be selected for use as the primary electrode combination, and orthogonally oriented electrodes 902A and 902B can be selected for use as the secondary electrode combination. Similarly, electrodes 904A and 904B can be selected for use as the primary electrode combination, and orthogonally oriented electrodes 903A and 903B can be selected for use as the secondary electrode combination. Other pairs and groups of electrodes can be selected to form primary and second electrode combinations, including combinations that utilize one or more housing electrodes (e.g., can or indifferent electrodes).

Figure 10:
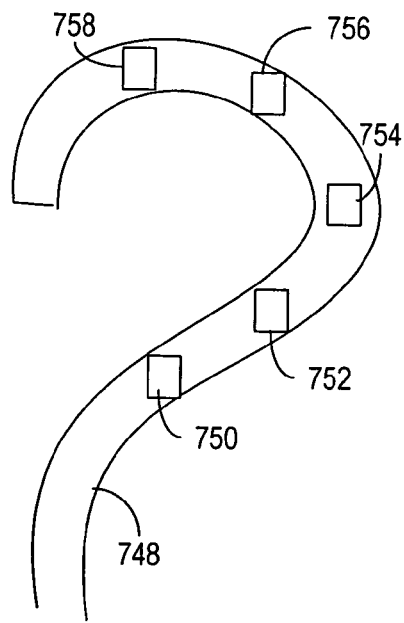
FIG. 10 is yet another multi-element noise canceling electrode configuration in accordance with the present invention.
Figure 11:
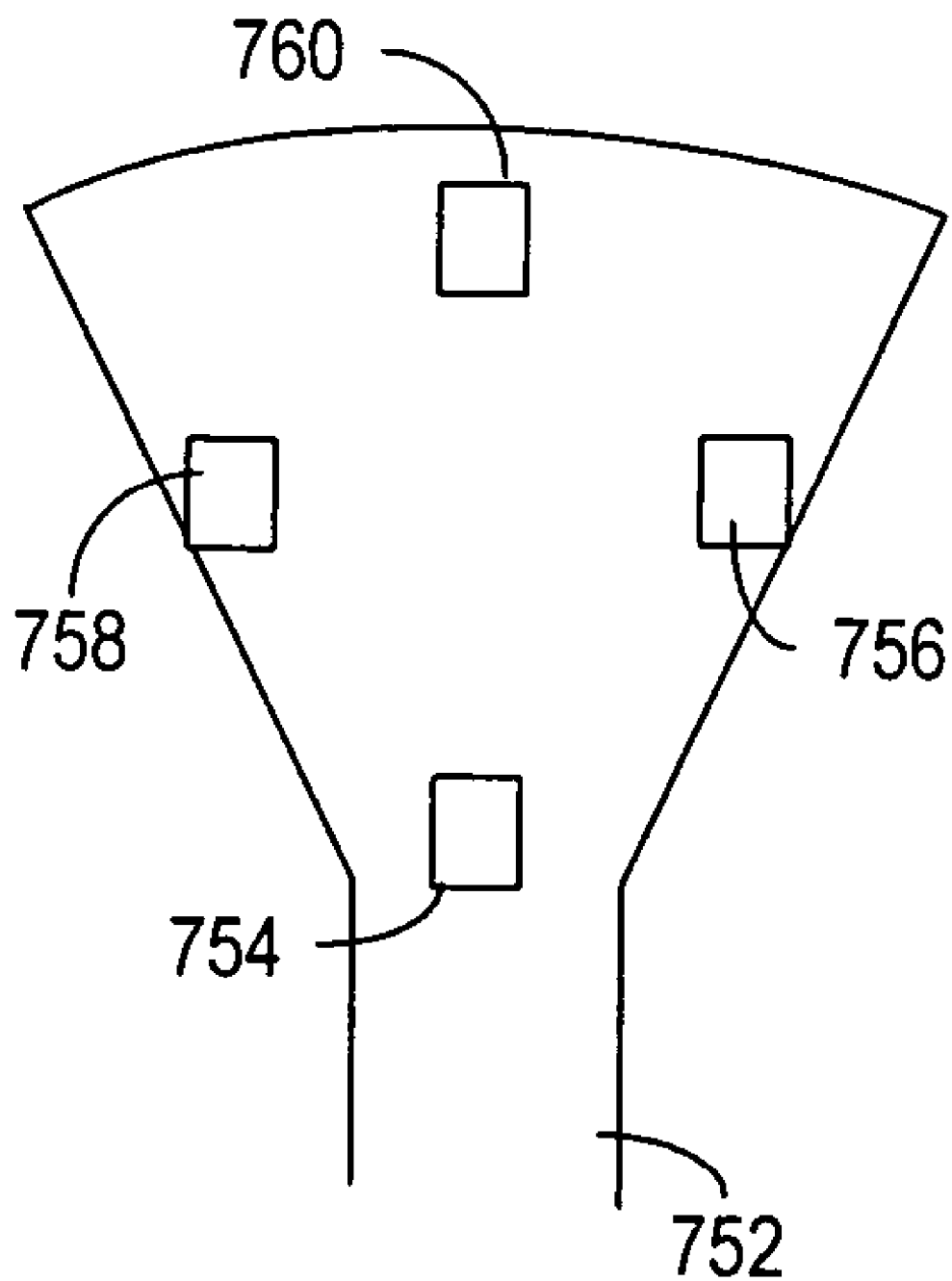
FIG. 11 is a further multi-element noise canceling electrode configuration in accordance with the present invention.

FIGS. 10 and 11 illustrate other electrode support configurations and electrode arrangements from which primary and secondary electrode combinations can be selected or defined. FIG. 10 illustrates a hook electrode configuration and FIG. 11 illustrates a spatula electrode configuration. Electrodes may be located on top and/or bottom surfaces of the electrode support, as well as internally located, to provide electrode configurations oriented along some or all three Cartesian axes.

In FIG. 10, a hook-shaped lead 748 includes electrodes 750, 752, 754, 756 and 758 located along the length of the hook-shaped lead 748. In FIG. 11, a lead 752 is illustrated with electrodes 754, 756, 758 and 760. The electrodes are illustrated spatially diverse in an orthogonal arrangement, but may be positioned in any useful arrangement or shape.

Figure 13:
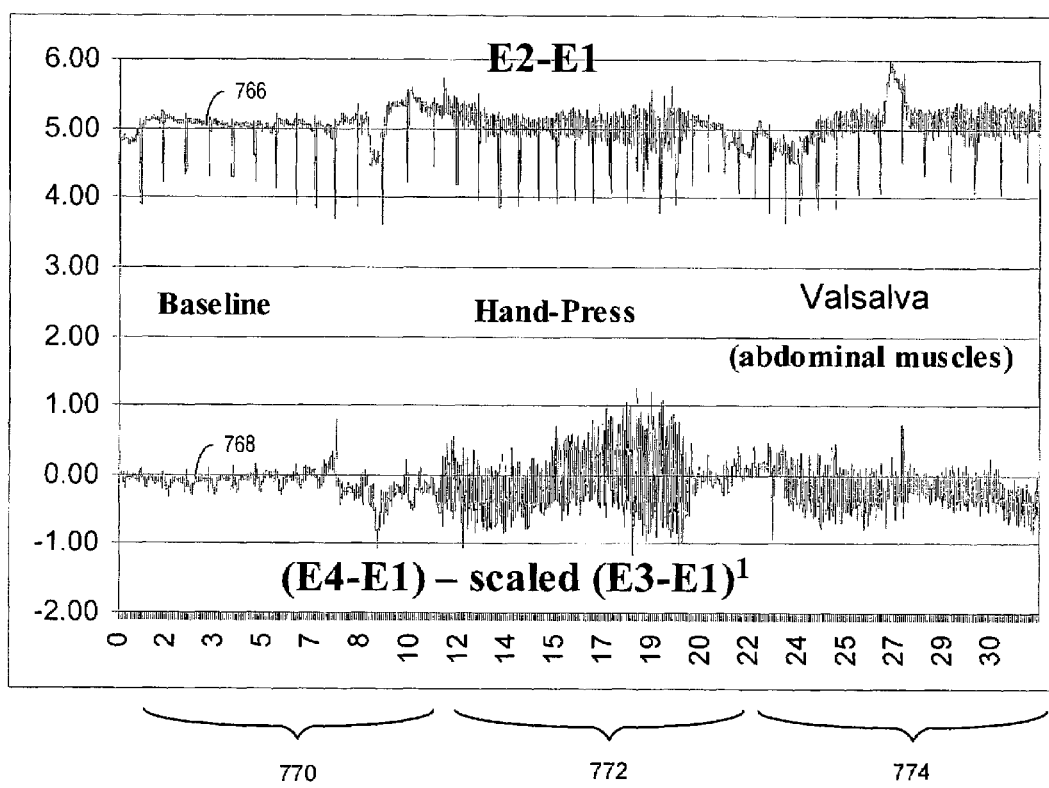
FIG. 13 illustrates signal plots derived from the electrode arrangement of FIG. 3.

Various illustrative sense vector waveforms developed from combinations of electrodes associated with some of the electrode configurations described above are provided in FIGS. 12 and 13. The "noise" in certain Figures was generated in one of two ways: via hand-press or valsalva mechanisms. FIGS. 12 and 13 illustrate sense vector waveforms developed using two particularly effective configurations for preferentially sensing cardiac and non-cardiac (e.g., noise) activity.

The electrode configuration associated with the sense vector waveform shown in FIG. 12 is that depicted in FIG. 6. The electrode configuration associated with the sense vector waveform shown in FIG. 13 is that depicted in FIG. 3. In each of these figures, it can be readily seen that the subject electrode configuration and sense vectors provide for a high degree of preferential sensing of cardiac and non-cardiac activity.

The graph of FIG. 12 has time as its ordinate and signal amplitude as its abscissa. The signal amplification is equal in both traces. Three events are noted on the ordinate; a base-line 776, a hand-press event 778, and a valsalva event 780. A trace 764 is representative of the signal received from the shielded electrode 732 (E3) in FIG. 6. Because the electrode 732 is shielded from a direct cardiac electrical path, non-cardiac activity dominates the trace 764.

A top trace 762 is representative of a linear combination of electrode signals providing a high SNR for the cardiac signal. The trace 762 is generated by subtracting signal E1 from signal E2. This can be expressed mathematically as:

Trace 762=$E2-E1$

It is apparent in trace 762 that the noise signals from the hand-press event 778 and valsalva event 780 are significantly attenuated as compared with the cardiac signal. In contrast, the signal in trace 764 is dominated by noise from hand-press event 778.

Referring now to another illustrative example, the graph of FIG. 13 has time as its ordinate and signal amplitude as its abscissa. The signal amplification is again equal for both traces. Three events are noted on the ordinate, a base-line 770, a hand-press event 772, and a valsalva event 774.

A trace 768 is representative of the signal received from a linear combination of electrode signals providing a noise reference (see FIG. 3). The trace 768 is generated by subtracting signal E1 (electrode 702) from both signal E4 (electrode 704) and signal E3 (electrode 708), scaling the E3 and E1 difference, and then subtracting the two resulting differences. This can be expressed mathematically as:

Trace 768=$(E4-E1)-(\text{Scale} \cdot (E3-E1))$

It should be noted that the electrodes are positioned, with respect to the heart, so that the E4−E1 and E3−E1 vectors are nearly adjacent and roughly parallel and therefore have nearly identical cardiac signal morphologies.

In this example, the E3−E1 term is scaled so that the average of the cardiac peaks of E3−E1 during the baseline are equal to the average of the cardiac peaks of E4−E1 during the baseline. Since both vectors have nearly the same cardiac signal properties, the cardiac signal nearly cancels in the difference, while having less cancellation effect on the noise signals. This provides for a good noise signal reference.

A top trace 766 is representative of a linear combination of electrode signals providing a high SNR for the cardiac signal. The trace 766 is generated by subtracting the electrode 702 signal E1 from the electrode 706 signal E2. This can be expressed mathematically as:

Trace 766=$(E2-E1)$

As is apparent in trace 766, the hand-press and valsalva events (noise) that dominate the signal of trace 768 are significantly attenuated, providing a clearer indication in trace 766 of the cardiac signal.

Figure 14:
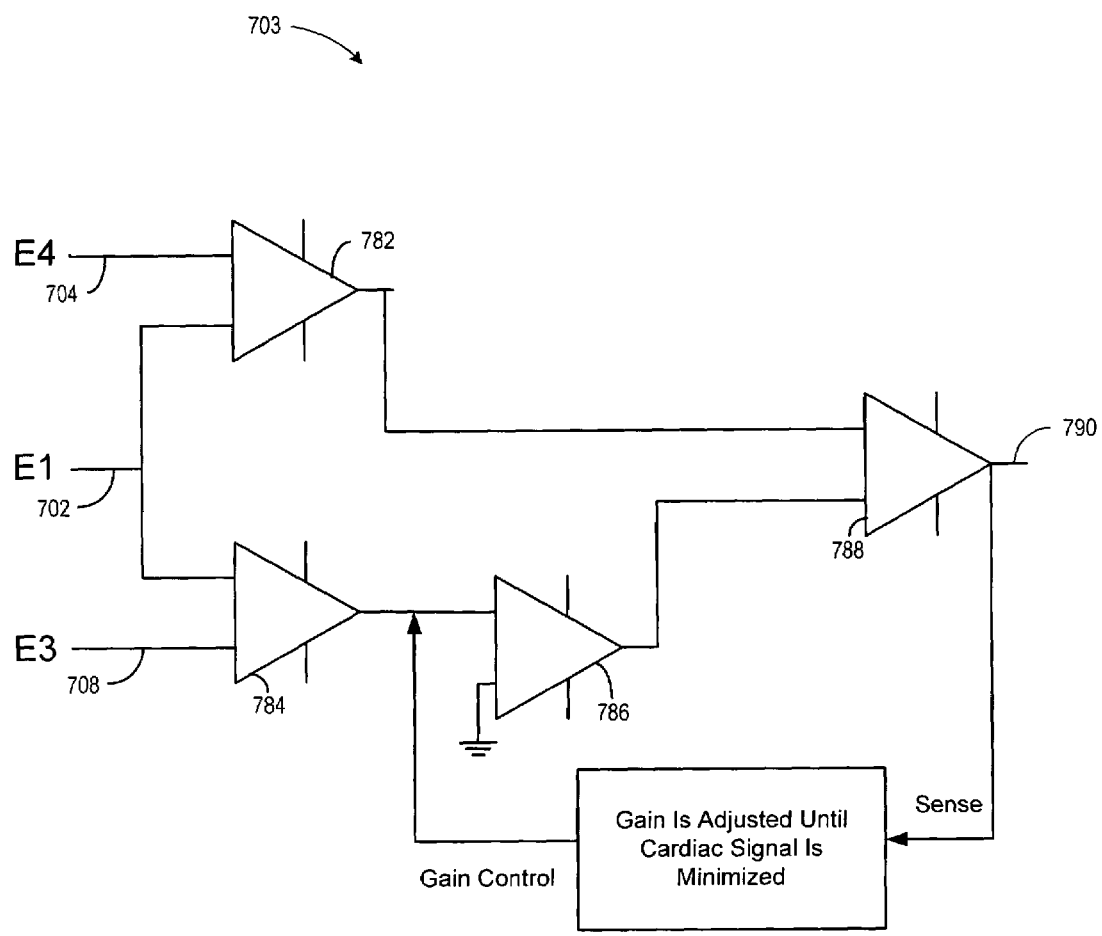
FIG. 14 is a circuit diagram of noise reduction circuitry in accordance with the present invention.

FIG. 14 is a diagram of a simplified analog circuit that can perform the electrode signal manipulation useful for providing the trace 768 of FIG. 13. The noise reduction block 703 includes a variable gain non-inverting amplifier 786, and three unity-gain difference amplifiers 782, 784, and 788. The difference amplifier 782 has as its inputs the signal E4 from the electrode 704 and the signal E1 from the electrode 702 (electrode configuration illustrated in FIG. 3). The output of difference amplifier 782 (E4-E1) is then input to the final difference amplifier 788.

The difference amplifier 784 has as its inputs the signal E3 from the electrode 708 and the signal E1 from the electrode 702. The output of difference amplifier (E3−E1) is input to the scaling amplifier 786, providing a scaled output {Scale·(E3−E1)} to the final difference amplifier 788. An output 790 of difference amplifier 788 provides the signal to generate the trace 768 of FIG. 13.

The circuit of FIG. 14 is illustrative of one embodiment consistent with the noise reduction block 203 illustrated in FIG. 1C. The noise reduction block 703, by way of the amplifiers used to perform the arithmetic operations with the electrode signals, may also perform the function of the sensing block 204 illustrated in FIG. 1C. Combining the functions of sensing block 204 and noise reduction block 203 may be useful to minimize the necessary componentry and lower the power requirements of the system.

Figure 15A:
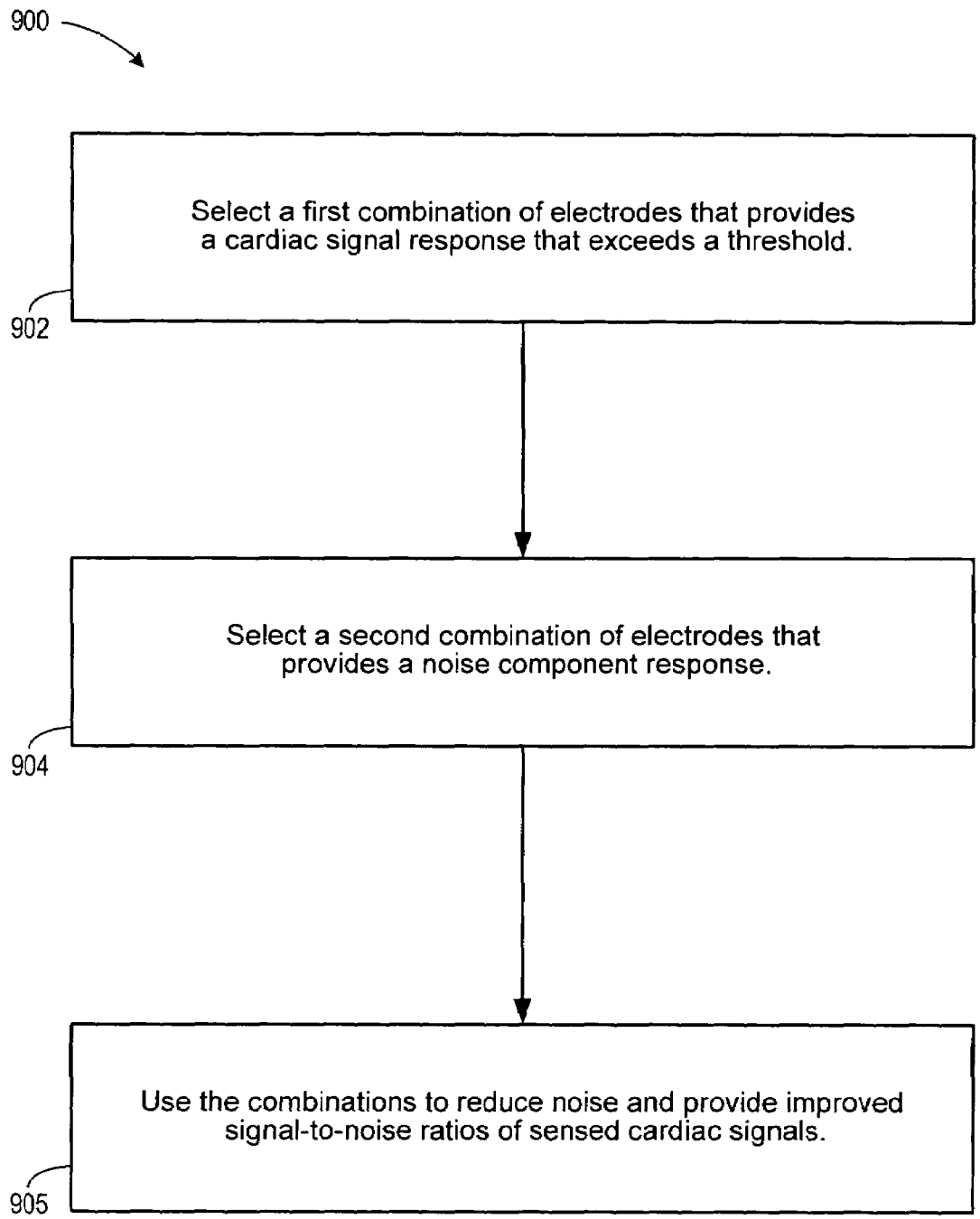
FIGS. 15A and 15B are flowcharts depicting cardiac SNR enhancing processes in accordance with the present invention.
Figure 15B:
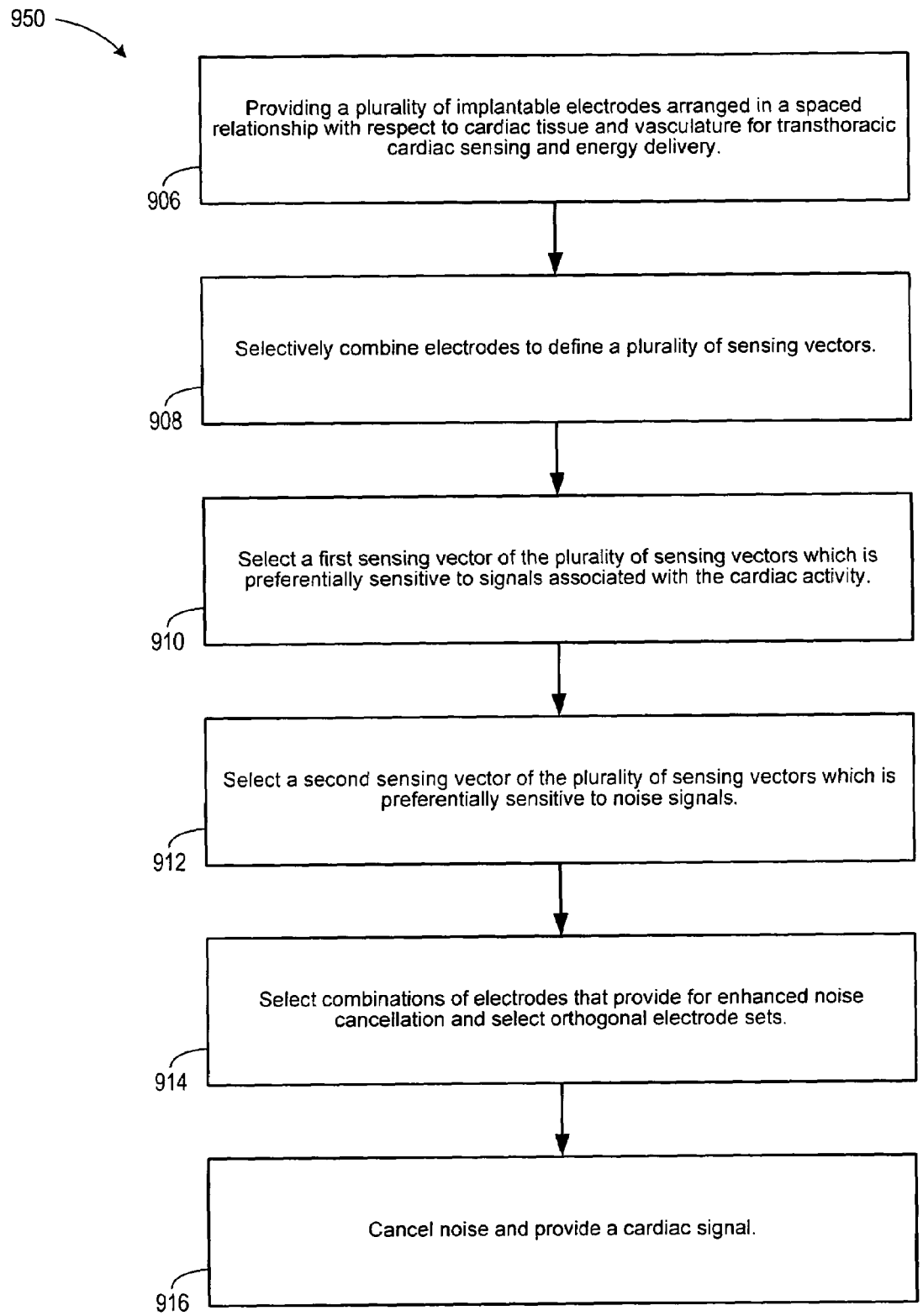

Referring now to FIGS. 15A and 15B, flowcharts are provided illustrating methods in accordance with the present invention. In FIG. 15A, a noise cancellation method 900 involves a controller selecting a first combination 902 of electrodes as an electrode combination that provides a cardiac signal response that exceeds a threshold. The controller selects a second combination 904 of electrodes as an electrode combination that provides a noise component response. The ICD may then use these combinations to reduce noise 905 and provide improved signal-to-noise ratios of sensed cardiac signals.

In the embodiment illustrated in FIG. 15B, a cardiac activity sensing method 950 involves providing a plurality of implantable electrodes, wherein each of the electrodes is arranged in a spaced relationship with respect to cardiac tissue and vasculature for transthoracic cardiac sensing and energy delivery 906. The electrodes are selectively combined to define a plurality of sensing vectors 908. The method further involves selecting a first sensing vector 910 of the plurality of sensing vectors, which is preferentially sensitive to signals associated with the cardiac activity, and selecting a second sensing vector 912 of the plurality of sensing vectors, which is preferentially sensitive to noise signals. The method may also involve selecting combinations 914 of electrodes that provide for enhanced noise cancellation and selecting orthogonal electrode sets. The method then involves canceling noise and providing a cardiac signal 916.

Still referring to FIGS. 15A and 15B, it is further contemplated that in addition to, or instead of, providing the improved cardiac signal 905 (FIG. 15A) or 916 (FIG. 15B), selected combinations of electrodes may be used to create two or more signals for further analysis. For example, a first electrode combination may be selected to provide an optimized cardiac signal, and a second electrode combination may be selected to provide a non-cardiac signal. The cardiac and non-cardiac signals may then be further analyzed to determine why arrhythmia activity was declared, and adjust therapy accordingly.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. An implantable cardiac device, comprising:
   a pulse generator comprising a controller configured to execute program instruction stored in memory, the pulse generator and the memory provided in a can configured for implantation;
   a rigid support structure coupled to, and spaced apart from, the can; and
   a plurality of implantable electrodes coupled to the pulse generator, the rigid support structure configured to maintain the plurality of implantable electrodes in respective subcutaneous extra-thoracic locations and in a spaced relationship with respect to cardiac tissue and vasculature, the plurality of electrodes comprising:
      a first combination of electrodes mounted to the support structure in a fixed spaced relationship along a first plane with respect to other electrodes of the plurality of implantable electrodes, the first electrode combination positioned on the support structure in a manner to preferentially sense a first type of signal relative to other electrodes of the plurality of implantable electrodes; and
      a second combination of electrodes mounted to the support structure in a fixed spaced relationship along a second plane with respect to other electrodes of the plurality of implantable electrodes, the second electrode combination positioned on the support structure in a manner to preferentially sense a second type of signal relative to the electrodes of the first electrode combination, wherein the first plane is in an orthogonal relationship with respect to the second plane and controller execution of the program instructions causes the implantable cardiac device to select one of the first combination of electrodes or the second combination of electrodes for sensing a cardiac signal as the first type or the second type of signal, select the other of the first combination of electrodes and the second combination of electrodes for sensing a noise signal as the other of the first type and the second type of signal, and remove content from the cardiac signal based on the content of the noise signal, the selection of the first combination of electrodes or the second combination of electrodes for sensing the cardiac signal and the other of the first combination of electrodes and the second combination of electrodes for sensing the noise signal based on a test performed using the plurality of electrodes.

2. The device of claim 1, wherein the can and the rigid support structure are maintained in a spaced apart relationship on opposite sides of the heart by a rigid elongated structure attached to the can and the support structure.

3. The device of claim 1, wherein the controller is configured such that the test comprises identifying a cardiac signal component and a noise component of signals acquired by each of the first combination of electrodes and the second combination of electrodes and comparing respective cardiac signal components and noise signal components between the first and second electrode combinations.

4. The device of claim 1, wherein the test comprises:
   controller selection of the first combination of electrodes or the second combination of electrodes for sensing the cardiac signal based on which electrode combination provides a cardiac signal response that exceeds a threshold; and
   controller selection of the first combination of electrodes or the second combination of electrodes for sensing the noise signal based on which electrode combination provides a noise component response.

5. The device of claim 1, wherein the test comprises:
   controller selection of the first combination of electrodes or the second combination of electrodes for sensing the cardiac signal based on which electrode combination provides a cardiac signal response that exceeds a signal-to-noise ratio threshold; and
   controller selection of the second combination of electrodes or the second combination of electrodes for sensing the noise signal based on which electrode combination provides a cardiac signal response substantially lower than the signal-to-noise ratio threshold.

6. The device of claim 1, wherein the test comprises:
controller selection of the first combination of electrodes or the second combination of electrodes for sensing the cardiac signal based on which electrode combination provides a cardiac signal response that exceeds a threshold; and
controller selection of the second combination of electrodes or the second combination of electrodes for sensing the noise signal based on which electrode combination provides a cardiac signal response substantially lower than the threshold.

7. The device of claim 1, wherein the cardiac device is configured such that the cardiac signals sensed by the selected first combination of electrodes or the second combination of electrodes comprise a cardiac signal component and a noise component, and the controller is further configured to execute stored program instructions to reduce the noise component of the cardiac signals using a noise component of the noise signals sensed by the other of the first combination of electrodes and second combination of electrodes subtracted from the cardiac signal.

8. The device of claim 1, further comprising:
a first electrode shield positioned on the cardiac device relative to the plurality of implantable electrodes to shield one or more electrodes of the second combination of electrodes from electrical cardiac activity with respect to at least one electrode of the first combination of electrodes; and
a second electrode shield positioned on the cardiac device relative to the plurality of implantable electrodes to shield one or more electrodes of the first combination of electrodes from electrical noise with respect to at least one electrode of the second combination of electrodes.

9. The device of claim 1, further comprising at least one electrode shield positioned on the cardiac device relative to the plurality of implantable electrodes to shield one or more electrodes of the second combination of electrodes from electrical cardiac activity with respect to at least one electrode of the first combination of electrodes.

10. The device of claim 1, wherein the cardiac device is configured such that the cardiac signals sensed by the selected first combination of electrodes or the second combination of electrodes comprise a cardiac component and a noise component, and the controller is configured to execute stored program instructions to linearly combine the sensed cardiac signals with the sensed noise signals sensed by the other of the first combination of electrode and the second combination of electrodes to reduce the noise component of the cardiac signals.

11. The device of claim 1, wherein the controller executes the stored program instructions such that:
the combination of electrodes selected to sense the cardiac signal is selected because during the test it provides a cardiac signal response that exceeds a signal-to-noise ratio threshold; and
the combination of electrodes selected to sense the noise signal is selected because during the test it provides a cardiac signal response substantially lower than the signal-to-noise ratio threshold.

12. The device of claim 1, wherein the controller executes the stored program instructions such that:
the combination of electrodes selected to sense the cardiac signal is selected because during the test it provides a cardiac signal response that exceeded a first signal-to-noise ratio threshold; and
the combination of electrodes selected to sense the noise signal is selected because during the test it provides a cardiac signal response lower than a second signal-to-noise ratio threshold.

13. The device of claim 1, wherein the controller executes the stored program instructions such that:
the combination of electrodes selected to sense the cardiac signal is selected because during the test it provides a cardiac signal response that exceeds a threshold; and
the combination of electrodes selected to sense the noise signal is selected because during the test it provides a cardiac signal response substantially lower than the threshold.

14. The device of claim 1, wherein the controller executes the stored program instructions such that:
the combination of electrodes selected to sense the cardiac signal is selected because during the test it provides a cardiac signal response that exceeds a first threshold; and
the combination of electrodes selected to sense the noise signal is selected because during the test it provides a cardiac signal response lower than a second threshold.

15. The device of claim 1, wherein the support structure is circular or elliptical in shape.

16. The device of claim 15, wherein the first electrode combination includes at least one electrode from the second electrode combination.

17. The device of claim 15, wherein the second electrode combination includes at least one electrode from the first electrode combination.

18. The device of claim 1, wherein the support structure is polygonal in shape.

19. The device of claim 1, wherein the support structure is curved in shape.

20. The device of claim 1, wherein the support structure is arrow shaped.

21. The device of claim 1, further comprising one or more tines provided on the support structure.

22. An implantable cardiac device, comprising:
a pulse generator comprising a controller configured to execute program instructions stored in memory, the pulse generator and the memory provided in a can configured for implantation;
a rigid support structure coupled to, and spaced apart from, the can; and
a plurality of implantable electrodes coupled to the pulse generator, the plurality of electrodes comprising:
a first combination of electrodes mounted to the support structure in a fixed spaced relationship with respect to other electrodes of the plurality of implantable electrodes, the first combination of electrodes positioned on the support structure in a manner to preferentially sense a first type of signal relative to other electrodes of the plurality of implantable electrodes; and
a second combination of electrodes, at least one of the electrodes of the second combination of electrodes mounted to the can in a fixed spaced relationship with respect to other electrodes of the plurality of implantable electrodes, the second combination of electrodes positioned on the cardiac device in a manner to preferentially sense a second type of signal relative to the electrodes of the first combination of electrodes, the support structure configured to maintain the first combination of electrodes in respective subcutaneous extra-thoracic locations and in a spaced relationship with respect to cardiac tissue and vasculature, wherein controller execution of the program instructions causes the implantable cardiac device to select one of the first combination of electrodes or the second combination of electrodes for sensing a cardiac signal as the first type or the second type of signal, select the other of the first combination of electrodes and the second combination of electrodes for sensing a noise signal as the other of the first type and the second type of signal, and remove content from the cardiac signal based on the content of the noise signal, the selection of the first combination of electrodes or the second combination of electrodes for sensing the cardiac signal and the other of the first combination of electrodes and the second combination of electrodes for sensing the noise signal based on a test performed using the plurality of implantable electrodes.

23. The device of claim 22, wherein the electrodes of the first combination of electrodes are arranged along a first plane and the electrodes of the second combination of electrodes are arranged along a second plane, and the first plane is orthogonal with respect to the second plane.

24. The device of claim 22, wherein the controller is configured to execute stored program instructions such that the test comprises identifying a cardiac signal component and a noise component of signals acquired by each of the first combination of electrodes and the second combination of electrodes and comparing the respective cardiac signal components and noise signal components between the first and second electrode combinations.

25. The device of claim 22, wherein the controller is configured to execute stored program instructions such that the test comprises:
   controller selection of the first combination of electrodes or the second combination of electrodes for sensing the cardiac signal based on which electrode combination provides a cardiac signal response that exceeds a threshold; and
   controller selection of the first combination of electrodes or the second combination of electrodes for sensing the noise signal based on which electrode combination provides a noise component response.

26. The device of claim 22, wherein the controller is configured to execute stored program instructions such that the test comprises:
   controller selection of the first combination of electrodes or the second combination of electrodes for sensing the cardiac signal based on which electrode combination provides a cardiac signal response that exceeds a signal-to-noise ratio threshold; and
   controller selection of the second combination of electrodes or the second combination of electrodes for sensing the noise signal based on which electrode combination provides a cardiac signal response substantially lower than the signal-to-noise ratio threshold.

27. The device of claim 22, wherein the first electrode combination includes at least one electrode from the second electrode combination.

28. The device of claim 22, wherein the second electrode combination includes at least one electrode from the first electrode combination.

29. The device of claim 22, wherein the controller is configured to execute stored program instructions and control the cardiac device such that the cardiac signals sensed by the selected first combination of electrodes or second combination of electrodes comprise a cardiac signal component and a noise component, and the controller is configured to execute stored program instructions to reduce the noise component of the cardiac signals using the noise signals sensed by the other of the first combination of electrodes and the second combination of electrodes.

30. The device of claim 22, wherein the controller is configured to execute stored program instructions and control the cardiac device such that the cardiac signals sensed by the selected first combination of electrodes or second combination of electrodes comprise a cardiac signal component and a noise component, and the controller is configured to execute stored program instructions to linearly combine the sensed cardiac signals with the noise signals sensed by the other of the first combination of electrode and the second combination of electrodes to reduce the noise component of the cardiac signals.

31. The device of claim 22, wherein the controller is configured to execute stored program instructions and control the cardiac device such that the cardiac signals sensed by the selected first combination of electrodes or second combination of electrodes comprise a cardiac signal component and a noise component, and the controller is configured to execute stored program instructions to select a therapy using the noise component.

32. The device of claim 22, wherein at least two electrodes of the first combination of electrodes are arranged in an orthogonal relationship with respect to at least two electrodes of the second combination of electrodes.

33. The device of claim 22, wherein the can and the support structure are maintained in a spaced apart relationship by a rigid elongated structure attached to the can and the support structure.

34. The device of claim 33, wherein the rigid elongated structure is configured to maintain the can and the support structure in a fixed relationship on opposing sides of the heart.

35. The device of claim 33, wherein the rigid elongated support structure can be distorted under manual force to take and maintain a desired shape.

36. The device of claim 22, further comprising at least one electrode shield positioned on the cardiac device relative to the plurality of implantable electrodes to shield one or more electrodes of the second combination of electrodes from electrical cardiac activity with respect to at least one electrode of the first combination of electrodes.

37. The device of claim 22, further comprising:
   a first electrode shield positioned on the cardiac device relative to the plurality of implantable electrodes to shield one or more electrodes of the second combination from electrical cardiac activity with respect to at least one electrode of the first combination; and
   a second electrode shield positioned on the cardiac device relative to the plurality of implantable electrodes to shield one or more electrodes of the first combination of electrodes from electrical noise with respect to at least one electrode of the second combination of electrodes.

38. The device of claim 22, wherein the support structure is circular or elliptical in shape.

39. The device of claim 22, wherein the support structure is polygonal in shape.

40. The device of claim 22, wherein the support structure is curved in shape.

41. The device of claim 22, wherein the support structure is arrow shaped.

42. The device of claim 22, further comprising one or more tines provided on the support structure.

* * * * *